United States Patent [19]

Osawa et al.

[11] Patent Number: 5,403,725
[45] Date of Patent: Apr. 4, 1995

[54] METHOD FOR PRODUCTION OF LYMPHOTOXIN (TNFB) IN CELL LINE A-C5-8

[75] Inventors: Toshiaki Osawa, Shin; Masuo Obinata, Sendai; Yoshiyuki Ishii, Chiba, all of Japan; Yoshio Kobayashi, Frederick, Md.

[73] Assignee: Denki Kagaku Kogyo Kabushiki Kaisha, Tokyo, Japan

[21] Appl. No.: 733,974

[22] Filed: Jul. 22, 1991

Related U.S. Application Data

[63] Continuation of Ser. No. 212,293, Jun. 27, 1988, abandoned, which is a continuation-in-part of Ser. No. 945,904, Dec. 23, 1986, abandoned.

[30] Foreign Application Priority Data

| Dec. 24, 1985 | [JP] | Japan | 60-289249 |
| Jun. 30, 1986 | [JP] | Japan | 61-151772 |
| Jun. 30, 1986 | [JP] | Japan | 61-151773 |
| Jun. 27, 1987 | [JP] | Japan | 62-160115 |

[51] Int. Cl.$^6$ .................... A61K 45/05; C12P 21/06; C12N 15/00
[52] U.S. Cl. .................. 435/69.5; 435/172.2; 435/240.26; 435/320.1; 424/85.1; 520/351; 935/10
[58] Field of Search ............ 530/23, 350, 389.1, 530/351, 385.7, 388.23, 389.2; 435/69.5, 172.2; 424/85.1, 320.1; 938/99, 240.26; 536/27

[56] References Cited

FOREIGN PATENT DOCUMENTS 164965 12/1985 European Pat. Off. ...... C12P 21/02

OTHER PUBLICATIONS

Asada et al. *Cell. Immunology* 1983 pp. 150–160 vol. 77 "Human T-Cell Hybridomas Producing Lymphokines".
Wallach et al. FEBS vol. 178(2) Dec. 1984 "Translation of mRNA for human lymphotoxin in microinjected Xenopus oocytes".
Gray et al. *Nature* vol. 312 Dec. 1984 pp. 721–727 "Cloning and expression of cDNA for human lymphotoxin, a lymphokine with tumor necrosis activity".
Kobayashi et al. *J. Biochem.* vol. 100 1986 pp. 727–733. *Journal of Biochemistry*, vol. 100, pp. 727–733 (1986).

Primary Examiner—David L. Lacey
Assistant Examiner—T. Michael Nisbet
Attorney, Agent, or Firm—Oblon, Spivak, McClelland, Maier, & Neustadt

[57] ABSTRACT

Lymphotoxin-producing human T-cell hybridomas are incubated in a medium containing phorbol myristate acetate, concanavalin-A or a mixture thereof, the resulting cells are fractionated by sucrose density-gradient centrifugation method to isolate a messenger RNA in 12.6S to 14.6S fractions, and a gene containing a part encoding a polypeptide having a lymphotoxin-activity is prepared from the messenger RNA. The gene is represented by the nucleotide sequence of the Table 1 as herein given. Using the present gene, a new lymphotoxin having the amino acid sequence (I) or (II) as given herein can be obtained by genetic engineering technology.

2 Claims, 6 Drawing Sheets

FIG. 5
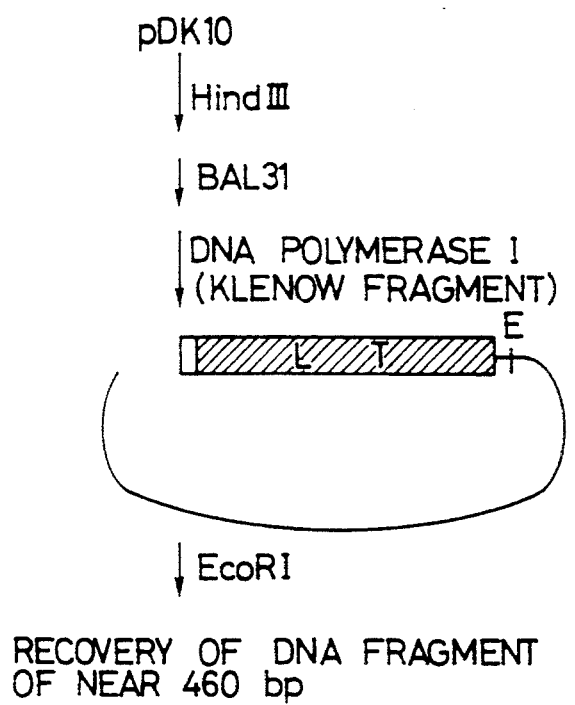
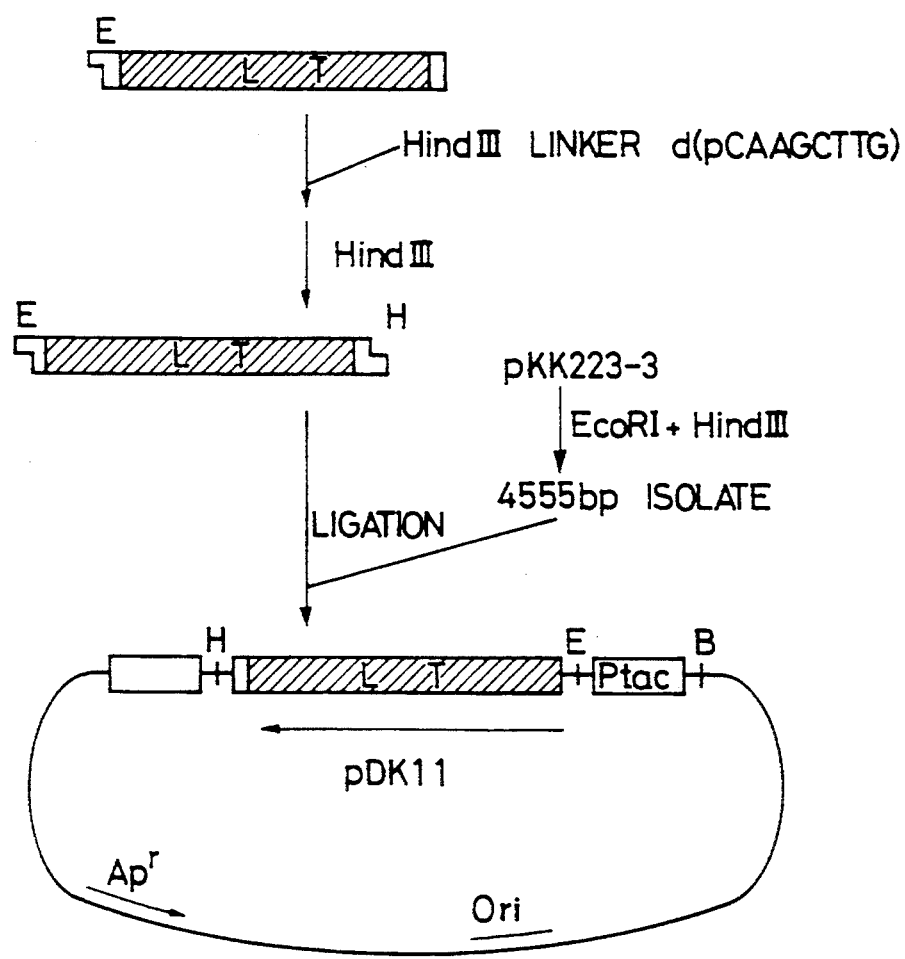

METHOD FOR PRODUCTION OF LYMPHOTOXIN (TNFB) IN CELL LINE A-C5-8

This application is a Continuation of application Ser. No. 07/212,293, filed on Jun. 27, 1988, which was a Continuation-In-Part of application Ser. No. 06/945,904, filed Dec. 23, 1986, both now abandoned.

BACKGROUND OF THE INVENTION

1. Field of the Invention

The present invention relates to a new gene, a part of which encodes a polypeptide having a lymphotoxin activity, a method for the production of the gene, and a human lymphotoxin produced from the gene by using genetic engineering technology.

The present invention also relates to an antitumor composition comprising the lymphotoxin as an active ingredient.

2. Description of the Background Art

Lymphotoxin (hereinafter referred to as LT) is known to be a kind of lymphokine which is specifically or non-specifically released from lymphocytes or established lymphoid cell lines and which has a cytotoxic activity. LT not only has a cytotoxic activity against various cancer cells but also an activity for intensifying the cytotoxic activity of certain kinds of carcinostatics or interferons, and it is expected to be usable as a tumoricidal agent or as other types of medicinal agents. (Refer to Granger G. A. et al., "International Congress of Chemotherapy", Kyoto, Japan, June 23–28, Abstracts, p. 15; and Matsunage K. et al., ibid, p. 352.)

For the production of a human LT, a variety of methods have been known where human-derived cells or human-derived tumor cells are cultured and the cultured supernatant liquid is purified to obtain the human LT. For instance, a method is known wherein tonsil cells or peripheral blood lymphocytes are cultured together with a phytohemagglutinin (hereafter referred to as PHA) and the human LT is isolated from the cultured supernatant liquid (refer to Peter, T. B. et al., J. Immunol., 111, 770 (1973); Walker, S. M. and Lucas, Z. J., J. Immunol., 109, 1233 (1972)). Another method is known wherein lymphoid tumor cells are cultured and the human LT is isolated from the cultured supernatant liquid (refer to Yamamoto, R. S. et al., J. Biol. Response Modifiers, 3, 76 (1984); European Patent Application No. 0100641). Yet another method is known wherein T-cell hybridomas are cultured in the presence of phorbol myristate acetate (hereinafter referred to as PMA) and/or concanavalin A (hereinafter referred to as Con A) and the human LT is isolated from the cultured supernatant liquid (refer to Asada, M. et al., Cell. Immunol., 77, 150 (1983)).

These known methods, however, have problems in that the content of LT contained in the culture supernatant solution is extremely small and the nutrient sources to be used in the cultivation (for example, fetal calf serum) are expensive. Therefore, economical production of LT of high purity is difficult by the known methods.

For the production of human LT, it would be desirable to have a means employing genetic engineering technology, wherein a gene corresponding to LT is inserted into a vector and the resulting recombinant plasmid is replicated, transcribed and translated in bacteria, fungi, yeasts or animal cells in order to obtain the desired human LT as produced in these cells.

The present inventors have previously obtained an LT-producing human T-cell hybridoma clone A-C5-8 cell line by the use of a human T-cell hybridization method (emetine/actinomycin-D method). (Refer to Asada, M., et al., Cell Immunol., 77, 150 (1983).) However, when the A-C5-8 cell line was cultured in the presence of Con A and PMA under the optimum LT-producing condition (incubation period of 30 hours or more), the messenger RNA (hereinafter referred to as mRNA) corresponding to LT could not be obtained, and therefore, the gene corresponding to LT could not be obtained. Thus, a need continues to exist for a method of producing LT by way of genetic engineering technology.

SUMMARY OF THE INVENTION

Accordingly, it is an object of the present invention to provide a gene encoding a polypeptide with LT activity as produced from an mRNA corresponding to LT.

It is a further object of this invention to provide a method for producing an LT gene encoding a polypeptide with LT activity.

It is yet another object of the present invention to provide large amounts of LT, which is produced from the LT gene encoding a polypeptide having LT activity.

These and other objects of the present invention as will hereinafter become more readily apparent have been accomplished by the studies of the present inventors.

The present inventors have investigated the conditions for obtaining the mRNA corresponding to LT, and as a result, have found that the mRNA corresponding to LT can be obtained by the incubation of A-C5-8 cell line together with PMA and/or Con A within 24 hours, preferably within 4 hours, and further have achieved the cloning of a new gene encoding a human LT-polypeptide by the application of the mRNA via genetic engineering technology and additionally have achieved the production of a new LT by the use of the cloned gene.

The present inventors further conducted intensive investigations and succeeded in producing the LT polypeptide in microorganisms transformed with a phenotypic expression vector with the cloned gene (cDNA) coding for the LT polypeptide being inserted therein. They further succeeded in recovering the human LT polypeptide substantially free of impurities from the thus-obtained human LT polypeptide-containing cultivation product. They confirmed that this human LT polypeptide can serve as an excellent therapeutic agent for malignant tumors.

Accordingly, the present invention provides a gene encoding a polypeptide with LT activity, a method for the production of the same and a new LT as obtained by the use of the gene.

More precisely, the present invention relates to a gene encoding a polypeptide with LT activity as produced from an mRNA which is isolated from a lymphokine-producing human T-cell hybridoma obtained by the incubation of the A-C5-8 cell line in a medium solution containing PMA and/or Con A within 24 hours, the mRNA being obtained as 12.6S to 14.6S fractions in the fractionation of sucrose density gradient centrifugation method, as well as mutants of the said gene including those of allele mutation, gene code degeneracy or partial modification, and a method for the production of the said gene. Mutants of the LT gene which fall within the scope of the present invention are especially those wherein the base sequence of Table 1 is altered such that the encoded amino acid sequence is not changed. Also included within the scope of the invention are genes including altered codons which encode polypeptides retaining the activity of LT. Such altered codons may encode conservative substitutions of amino acids (e.g. Ala for Gly, Ser for Thr, Leu for Val, etc.), or may be a small number (e.g. 1 to 3) of deleted codons.

The present invention is further concerned with a human LT polypeptide substantially free of impurities as obtained by cleaving the cDNA (Table 1) coding for the LT polypeptide with a restriction enzyme, ligating the cleaved cDNA with a phenotypic expression vector having a translation initiation site incorporated therein and cleaved beforehand with the same restriction enzyme, introducing the resulting phenotypic expression vector into an appropriate host, for example *Escherichia coli*, cultivating the thus-obtained transformant, and extracting and purifying the human LT polypeptide from the culture thus obtained.

The present gene has a nucleotide sequence as represented by Table 1:

BRIEF DESCRIPTION OF THE DRAWINGS

FIG. 1 is an outline showing the restriction endonuclease cleavage map of the working example of the present invention.

FIG. 2 is an outline showing the restriction endonuclease-cleaved sites as used for the determination of the nucleotide sequence and the directions and ranges for the determination of the base sequence in the working Example of the present invention.

In these drawings, B represents BamHI, E represents EcoRI, P represents PstI.

FIG. 3 shows steps for the formation of the tac promoter-containing phenotypic expressing plasmid pLT13tac6 in Example 5, where the arrows designate the direction of the action of the promoter.

FIG. 4 shows steps for the formation of tac promoter-containing phenotypic expressing plasmid pDK10 in Example 9, where the arrows designate the direction of the action of the promoter.

FIG. 5 shows steps for the formation of tac promoter-containing phenotypic expressing plasmid pDK11 in Example 9, where the arrows designate the direction of the action of the promoter.

TABLE 1

```
                    1                  20                       40                     60
                    CGGGCTCCTGCACCTGCTGCCTGGATCCCCGGCCTGCCTGGGCCTGGGCCTTGGTTCTCCCC
                      80                                  100                                  120
ATG ACA CCA CCT GAA CGT CTC TTC CTC CCA AGG GTG TGT GGC ACC ACC CTA CAC CTC CTC
                      140                                 160                                  180
CTT CTG GGG CTG CTG CTG GTT CTG CTG CCT GGG GCC CAG GGG CTC CCT GGT GTT GGC CTC
                      200                                 220                                  240
ACA CCT TCA GCT GCC CAG ACT GCC CGT CAG CAC CCC AAG ATG CAT CTT GCC CAC AGC AAC
                      260                                 280                                  300
CTC AAA CCT GCT GCT CAC CTC ATT GGA GAC CCC AGC AAG CAG AAC TCA CTG CTC TGG AGA
                      320                                 340                                  360
GCA AAC ACG GAC CGT GCC TTC CTC CAG GAT GGT TTC TCC TTG AGC AAC AAT TCT CTC CTG
                      380                                 400                                  420
GTC CCC ACC AGT GGC ATC TAC TTC GTC TAC TCC CAG GTG GTC TTC TCT GGG AAA GCC TAC
                      440                                 460                                  480
TCT CCC AAG GCC ACC TCC TCC CCA CTC TAC CTG GCC CAT GAG GTC CAG CTC TTC TCC TCC
                      500                                 520                                  540
CAG TAC CCC TTC CAT GTG CCT CTC CTC AGC TCC CAG AAG ATG GTG TAT CCA GGG CTG CAG
                      560                                 580                                  600
GAA CCC TGG CTG CAC TCG ATG TAC CAC GGG GCT GCG TTC CAG CTC ACC CAG GGA GAC CAG
                      620                                 640                                  660
CTA TCC ACC CAC ACA GAT GGC ATC CCC CAC CTA GTC CTC AGC CCT AGT ACT GTC TTC TTT
                      680                      700                     720
GGA GCC TTC GCT CTG TAG AACTTGGAAAAATCCAGAAA GAAAAAATAATTGATTTCAAGACCTTCTCCCCAT
     740                     760                      780                      800
TCTGCCTCCATTCTGACCATTTCAGGGGTCGTCACCACCTCTCCTTTGGCCATTCCAACAGCTCAAGTCTTCCCTGATC
      820                     840                     860                      880
AAGTCACCGGAGCTTTCAAAGAAGGAATTCTAGGCATCCCAGGGGACCACACCTCCCTGAACCATCCCTGATGTCTG
          900                     920                     940                      960
TCTGGCTGAGGATTTCAAGCCTGCCTAGGAATTCCCAGCCCAAAGCTGTTGGTCTTGTCCACCAGCTAGGTGGGGCC
               980                      1000                    1020
TAGATCCACACACAGAGGAAGAGCAGGCACATGGAGGAGCTTGGGGGATGACTAGAGGCAGGGAGGGGACTA
1040                   1060                     1080                    1100
TTTATGAAGGCAAAAAAATTAAATTATTTATTTATGGAGGATGGAGAGAGGGAATAATAGAAGAACATCCAAGGAG
     1120                     1140                     1160                     1180
AAACAGAGACAGGCCCAAGAGATGAAGAGTGAGAGGGCATGCGCACAAGGCTGACCAAGAGAGAAAGAAGTAGG
            1200                    1220                    1240                     1260
CATGAGGGATCACAGGGCCCCAGAAGGCAGGGAAAGGCTCTGAAAGCCAGCTGCCGACCAGAGCCCCAAACGGA
                  1280                    1300      1310
GGCATCTGCATCCTCGATGAAGCCCAATAAACCTCTTTTCTCCCCCT
MET THR PRO PRO GLU ARG LEU PHE LEU PRO ARG VAL CYS GLY THR THR LEU HIS LEU LEU
LEU LEU GLY LEU LEU LEU VAL LEU LEU PRO GLY ALA GLN GLY LEU PRO GLY VAL GLY LEU
THR PRO SER ALA ALA GLN THR ALA ARG GLN HIS PRO LYS MET HIS LEU ALA HIS SER ASN
LEU LYS PRO ALA ALA HIS LEU ILE GLY ASP PRO SER LYS GLN ASN SER LEU LEU TRP ARG
ALA ASN THR ASP ARG ALA PHE LEU GLN ASP GLY PHE SER LEU SER ASN ASN SER LEU LEU
VAL PRO THR SER GLY ILE TYR PHE VAL TYR SER GLN VAL VAL PHE SER GLY LYS ALA TYR
SER PRO LYS ALA THR SER SER PRO LEU TYR LEU ALA HIS GLU VAL GLN LEU PHE SER SER
GLN TYR PRO PHE HIS VAL PRO LEU LEU SER SER GLN LYS MET VAL TYR PRO GLY LEU GLN
GLU PRO TRP LEU HIS SER MET TYR HIS GLY ALA ALA PHE GLN LEU THR GLN GLY ASP GLN
LEU SER THR HIS THR ASP GLY ILE PRO HIS LEU VAL LEU SER PRO SER THR VAL PHE PHE
GLY ALA PHE ALA LEU
```

FIG. 6 shows steps for the formation of tac promoter-containing phenotypic expressing plasmid pDK12 in Example 9, where the arrows designate the direction of the action of the promoter.

DETAILED DESCRIPTION OF THE PREFERRED EMBODIMENTS

Figure 1:

There are some reports by Gray, P. W. et al (Nature, 312, 721 (1984)) and by Nedwin, G. E. et al (Nucleic Acids Research, 13, 6361 (1985)) on the base sequence of the gene encoding the polypeptide with human LT-activity. Gray et al. formed LT-cDNA, using mRNA as extracted and purified from human peripheral blood mononuclear cells (hereinafter referred to as PBMC) as activated with PMA, Staphylococcal enterotoxin-B and thymosin α1 for 48 hours. Nedwin et al. obtained a PBMC gene capable of being hybridized with Gray et al's gene, by screening a recombinant human-λ library by means of hybridization method using $^{32}$P-labeled DNA encoding the 34 amino-terminal residues of Gray et al's LT. As shown in the following Table 2, the LT-gene of the present invention differs from Gray et al's PBMC-cDNA by 14 nucleotides in four positions and differs from Nedwin et al's PBMC-gene by 9 nucleotides in two positions. In addition, it is noted that Nedwin et al's PBMC-gene contains an intron of 247 nucleotides between the 267th base and the 268th base.

Regarding the method for the production of the gene, Gray et al. extracted and purified the mRNA from the cells as obtained by the incubation of non-adhesive cells of human peripheral blood lymphocytes in the presence of PMA, staphylococcal enterotoxin B and thymosin α1 for 48 hours and produced the gene from the resulting mRNA; while the present inventors extracted and purified the mRNA from the cells as obtained by the incubation of LT-producing human T-cell hybridoma in the presence of PMA and/or Con A for 0.5 to 5 hours and produced the gene from the resulting mRNA.

TABLE 2

Comparison of base sequences in LT-gene of the present invention, PBMC-derived LT-gene and recombinant human-λ library-derived LT-gene:

| A-C5-8 cDNA[a] | PBMC cDNA[b] | PBMC gene[c] |
|---|---|---|
| CGGG 14 | GGTC | GGTG |
| AAC (Asn) 240 | ACC (Thr) | AAC (Asn) |
| ACAC 862 | CACA | ACAC |
| CCCCT 1306 | TGAAA | TGAAA |

[a]Present Invention
[b]Gray et al.
[c]Nedwin et al.

For the confirmation of the LT-activity expression of the gene (A-C5-8 cDNA) of the present invention, the cloned DNA was treated with restriction enzymes and then inserted into a pertinent phenotypic expression vector to obtain an LT-producing plasmid the resulting plasmid was introduced into *Escherichia coli* and animal cells for the transduction thereof and the production of LT by these cells was confirmed.

LT each having the following amino acid sequence (I), (II) or (III) can be obtained as mentioned below. (The LT each having the amino acid sequence (I), (II) or (III) is hereinafter referred to as LT(I), LT(II) or LT(III), respectively.)

Amino acid sequence (I):

MET ASP PRO ALA GLN THR ALA ARG GLN HIS
PRO LYS MET HIS LEU ALA HIS SER ASN LEU
LYS PRO ALA ALA HIS LEU ILE GLY ASP PRO
SER LYS GLN ASN SER LEU LEU TRP ARG ALA
ASN THR ASP ARG ALA PHE LEU GLN ASP GLY
PHE SER LEU SER ASN ASN SER LEU LEU VAL
PRO THR SER GLY ILE TYR PHE VAL TYR SER
GLN VAL VAL PHE SER GLY LYS ALA TYR SER

PRO LYS ALA THR SER SER PRO LEU TYS LEU
ALA HIS GLU VAL GLN LEU PHE SER SER GLN
TYR PRO PHE HIS VAL PRO LEU LEU SER SER
GLN LYS MET VAL TYR PRO GLY LEU GLN GLU
PRO TRP LEU HIS SER MET TYR HIS GLY ALA
ALA PHE GLN LEU THR GLN GLY ASP GLN LEU
SER THR HIS THR ASP GLY ILE PRO HIS LEU
VAL LEU SER PRO SER THR VAL PHE PHE GLY
ALA PHE ALA LEU

Amino acid sequence (II)

MET HIS LEU ALA HIS SER ASN LEU LYS PRO
ALA ALA HIS LEU ILE GLY ASP PRO SER LYS
GLN ASN SER LEU LEU TRP ARG ALA ASN THR
ASP ARG ALA PHE LEU GLN ASP GLY PHE SER
LEU SER ASN ASN SER LEU LEU VAL PRO THR
SER GLY ILE TYR PHE VAL TYR SER GLN VAL
VAL PHE SER GLY LYS ALA TYR SER PRO LYS
ALA THR SER SER PRO LEU TYR LEU ALA HIS

GLU VAL GLN LEU PHE SER SER GLN TYR PRO
PHE HIS VAL PRO LEU LEU SER SER GLN LYS
MET VAL TYR PRO GLY LEU LEU GLN PRO TRP
LEU HIS SER MET TYR HIS GLY ALA ALA PHE
GLN LEU THR GLN GLY ASP GLN LEU SER THR
HIS THR ASP GLY ILE PRO HIS LEU VAL LEU
SER PRO SER THR VAL PHE PHE GLY ALA PHE
ALA LEU

Amino acid sequence (III)

1                  10
MET HIS LEU ALA SER ASN LEU LYS PRO ALA
                       20
ALA HIS LEU ILE GLY ASP PRO SER LYS GLN
                       30
ASN SER LEU LEU TRP ARG ALA ASN THR ASP
                       40
ARG ALA PHE LEU GLN ASP GLY PHE SER LEU
                       50
SER ASN ASN SER LEU LEU VAL PRO THR SER
                       60
GLY ILE TYR PHE VAL TYR SER GLN VAL VAL
                       70
PHE SER GLY LYS ALA TYR SER PRO LYS ALA

-continued

| | | | | | | | | 80 |
|---|---|---|---|---|---|---|---|---|
| THR | SER | SER | PRO | LEU | TYR | LEU | ALA | HIS GLU |
| | | | | | | | | 90 |
| VAL | GLN | LEU | PHE | SER | SER | GLN | TYR | PRO PHE |
| | | | | | | | | 100 |
| HIS | VAL | PRO | LEU | LEU SER | SER | GLN LYS | MET |
| | | | | | | | | 110 |
| VAL | TYR | PRO | GLY | LEU | GLN | GLU | PRO | TRP LEU |
| | | | | | | | | 120 |
| HIS | SER | MET | TYR | HIS | GLY | ALA | ALA | PHE GLN |
| | | | | | | | | 130 |
| LEU | THR | GLN | GLY | ASP | GLN | LEU | SER | THR HIS |
| | | | | | | | | 140 |
| THR | ASP | GLY | ILE | PRO | HIS | LEU | VAL | LEU SER |
| | | | | | | | | 150 |
| PRO | SER | THR | VAL | PHE | PHE | GLY | ALA | PHE ALA |
| LEU | | | | | | | | |

The A-C5-8-cDNA (see the above Table 1) is cleaved with restriction enzymes. On the other hand, a phenotypic expression vector to which a translation-initiation site has been introduced is cleaved with the same restriction enzymes. These are ligated to obtain a phenotypic expression plasmid for LT-production, and the resulting plasmid is introduced into a pertinent host such as *Escherichia coli* to obtain a transformant. The resulting transformant is cultured and culture broth or transformant is extracted and purified to obtain the desired LT, which does not contain substantial amounts of any impurities.

As shown in the following Table 3, both the LT(I) and LT(II) of the present invention are different from the known LT (Gray, P. W. et al., Nature, 312, 721 (1984)) in the molecular structures thereof, in that the LT(I) is lacking in 10 N-terminal amino acids in the known LT but is bonded with Met-Asp-Pro-bond and that the LT(II) is lacking in 19 N-terminal amino acids in the known LT.

Also, Aggarwal, B. B. et al [Journal of Biological Chemistry, 260, 2334 (1985)] described that two LTs derived from the human lymphoblast cell line RPMI 1788 have molecular weights of 20,000 and 25,000, respectively. The 6th amino acid residue (ASN) in the amino acid sequence (III) and the N-terminal amino acid composition of the LT polypeptide according to the invention differ from those in said two LTs. Thus, in the above-mentioned LT having a molecular weight of 20,000, the terminal amino acid HIS is the counterpart of the N-terminal amino acid sequence

```
1            4
MET—HIS—LEU—ALA
``` in amino acid sequence (III). In the LT having a molecular weight of 25,000, the counterpart to the N-terminal amino acid sequence

```
1            4
MET—HIS—LEU—ALA
``` in sequence (III) is LEU-PRO-GLY-VAL-GLY-LEU-THR-PRO-SER-ALA-ALA-GLN-THR-ALA-ARG-GLN-HIS-PRO-LYS-MET-HIS-LEU-ALA-HIS. The three LT polypeptides thus differ from one another on the molecular level.

When a gene is expressed in *Escherichia coli*, an extra methionine residue addition to the N-terminus generally occurs, and this may cause adverse effects, such as antigenicity, in applying the expression product as a drug. In accordance with the invention, the 222nd to 224th nucleotides (ATG) shown in Table 1 are used as the initiation codon, so that an extra methionine residue addition can be avoided.

The known lymphotoxins are disadvantageous in that the N-terminal portion is unstable and readily undergoes cleavage during cultivation, purification and/or storage and, therefore, further purification is required for obtaining an LT polypeptide having the desired amino acid sequence although the cleavage product polypeptide retains LT activity. In other words, it is difficult to obtain them as homogeneous products. Presumable causes for such cleavage in the N-terminal portion are cleavage due to a protease which is secreted intracellularly during cultivation and/or cell harvesting and cleavage due to various factors present during purification steps and storage, for example proteases, heat, pH, ionic strength, interaction with resin, solvent and mechanical shearing force. Therefore, an LT polypeptide stable to the cleavage factors mentioned above and having no sign of cleavage in the N-terminal portion is desired.

As compared with a different LT (EP-application 0100641) obtained by incubation of lymphoid tumor cells followed by isolation from the cultured supernatant liquid, LT(I) is superior as having a higher pH stability and in addition, has a different isoelectric point.

TABLE 3

Comparison between LT of the present invention and known LT in N-terminal amino acid-sequences:

| Amino acid sequence (I) | Amino acid sequence (II) | Amino acid sequence (III) | Gray, et al. |
|---|---|---|---|
| | | | (MET) |
| | | | Leu |
| | | | Pro |
| | | | Gly |
| | | | Val |
| | | | Gly |
| | | | Leu |
| (N-terminal) | | | Thr |
| Met | | | Pro |
| Asp | | | Ser |
| Pro | | | Ala |
| Ala | | | Ala |
| Gln | | | Gln |
| Thr | | | Thr |
| Ala | | | Ala |
| Arg | | | Arg |
| Gln | | | Gln |
| His | | | His |
| Pro | | | Pro |
| Lys | | | Lys |
| Met | Met | | Met |
| His | His | Met | His |
| Leu | Leu | His | Leu |
| Ala | Ala | Leu | Ala |
| His | His | Ala | His |
| Ser | Ser | Ser | Ser |
| Asn | Asn | Asn | Thr |
| Leu | Leu | Leu | Leu |

In general, when a genetic product is obtained by the use of recombinant microorganisms, the product obtained has a structure containing an unnecessary methionine at the the N-terminal of the product obtained from a natural type gene. However, the LT(II) of the present invention does not contain any unnecessary methionine, and therefore, it has structure which is very similar to the natural type product. Moreover, LT(II) is very safe to use.

The present invention will be explained in greater detail hereinafter.

(1) Selection of Cells of High LT-productivity As the LT-producing cells, there can be used normal human lymphocytes, established human T-lymphoid cell lines such as CCRF-CEM, MOLT-4F and JURKAT and cloned cell lines thereof as well as established human B-lymphoid cell lines such as RPMI-1788. In particular, an LT-producing human T-cell hybridoma as obtained by cell fusion of normal human T-lymphocytes and established human T-lymphoid cells are preferably used, as these have high LT-productivity and subcultivation of the cells is possible. The LT-producing human T-cell hybridomas have a higher LT-productivity than the parent cells of established human T-lymphoid cells, and therefore, a large amount of mRNA may be extracted and isolated from the cells.

The analysis to measure the LT activity was carried out in accordance with the method of Kobayashi Y., et al. (J. Immunol., 122, 791 (1979)). In this measurement, the cytotoxic activity of a sample from a supernatant of cultured cells or an extract from cultured cells against mouse L·P3 cells (sub-line of L-cells) was defined as an index. One unit/ml of LT was designated by the concentration thereof to kill 50% of the target cells.

The LT-producing human T-cell hybridoma can be obtained by a known method (Japanese Patent Application (OPI) No. 72520/83). (The term "OPI" as used herein means an "unexamined and published application".)

For instance, the human T-lymphoid tumor cells are treated with a protein synthesis-inhibitor or with a combination of the inhibitor and an RNA synthesis inhibitor, and on the other hand, human T-lymphocytes are stimulated with a mitogen or an antigen, and then both are hybridized in the presence of a hybridization-accelerator (such as polyethylene glycol), and the resultant hybridized cells (human T-cell hybridoma cells) are isolated. The thus obtained human T-cell hybridomas are incubated in a culture medium (for example, a culture medium obtain by adding 10% of fetal calf serum, $5 \times 10^{-5}M$ of 2-mercaptoethanol and 2 mM of glutamine to a minimal medium of RPMI 1640, which is hereinafter referred to as RPMI medium) at 37° C. under an atmosphere of $CO_2(5\%)$air(95%), and then, the above-mentioned LT-producing human T-cell hybridomas are screened.

(2) Incubation of Cells

In order to obtain mRNA from the LT-producing human T-cell hybridomas, at least $10^9$ or more cells are required, and these cells are generally obtained by incubation of the resulting hybridomas. For instance, the cells are put in a nutrient medium in an amount of $10^5$ to $10^7$ cells/ml, and these are incubated in a laboratory dish as set in a flask-rotatory incubator for tissue-incubation (spinner flask) at 37° C. in an atmosphere of $CO_2(5\%)$-air(95%).

The incubation time varies, depending upon the composition of the medium and the initial cell concentration, and is, in general, appropriately 1 to 5 days. After incubation, the culture solution is centrifuged to isolate the cells.

The nutrient medium can be selected from a minimal medium containing one or more ingredients selected from saccharides, amino acids, vitamins, hormones, proteins, antibiotics, growth factors and inorganic bases or a medium comprising the minimal medium and an animal serum added thereto.

Commercial RPMI 1640 medium, MEM medium, Dulbecco's modified MEM medium, etc. can also be used as the minimal medium.

Regarding the animal serum, a fetal calf serum, a calf serum, a horse serum, a human serum or the like can be added to the minimal medium in an amount of 1 to 20% of the medium.

In addition, the cells can be proliferated in nude mouse, hamster or other warm blood animals except human.

(3) Propagation of mRNA

The LT-producing human T-cell hybridomas obtained in (2) above are put in a nutrient medium in an amount of $10^6$ to $10^7$ cells/ml and PMA and/or Con A is(are) added thereto and thus, when the cells are incubated they produce a larger amount of mRNA corresponding to LT. The preferred concentration of PMA is 20 to 200 ng/ml, and the preferred concentration of Con A is 5 to 50 μg/ml.

The incubation time is within 24 hours, preferably within 8 hours. This is because the content of mRNA corresponding to the LT activity in the cultured cells decreases with the lapse of time. In particular, if the incubation time exceeds 24 hours, the best period for the recovery of LT from the supernatant of the culture medium after the incubation of the LT-producing human T-cell hybridomas therein is 24 to 72 hours, and the amount of the mRNA corresponding to the LT in the cultured cells becomes extremely small in such period, and thus, the recovery of the mRNA is difficult. The method for establishing of the cell line of the LT-producing human T-cell hybridoma A-C5-8 cell line to be used in the present invention and the properties thereof are described in known publications. (Refer to Asada, M. et al., Cellular Immunology, 77, 150 (1983).)

(4) Extraction of Total Cellular RNA from Cells

The extraction of the total cellular RNA from the cells obtained in (3) above can be carried out in accordance with a guanidine hydrochloride method (Deeley, R. G. et al., J. Biol. Chem., 252, 8310 (1977)) or a similar known method.

For instance, the cells ($10^9$ or more cells) as obtained in (3) above are suspended in a homogenate-buffer (containing 8M of guanidine hydrochloride, 5 mM of dithiothreitol and 20 mM of sodium acetate, and regulated to have pH of 7 with NaOH) and homogenized in a homogenizer or the like. A complete nucleic acid fraction is extracted from the resulting homogenate material by ethanol-precipitation or phenol-extraction, and then the total cellular RNA recovered therefrom by lithium chloride-precipitation. In the extraction operation, it is preferred that the pieces of equipment to be used are dry-heated or treated with diethyl pyrocarbonate and then sterilized in an autoclave and that the operators have vinyl plastic gloves on their hands during the operation, in order to prevent the decomposition of the RNA by the action of RNase.

(5) Isolation of mRNA from Total Cellular RNA

Isolation of the desired mRNA from the complete RNA can be carried out by means of conventional methods including sucrose density-gradient centrifugation method, gel-filtration method, electrophoresis method, membrane-filter method or oligo-dT-cellulose chromatography method, or by a combination of these methods.

For the confirmation of the mRNA thus obtained to be the desired LT-encoding mRNA, the obtained mRNA is translated into a protein and the biological activity thereof is checked. For instance, the mRNA is injected into or added to a pertinent protein-synthesis system such as oocytes of *Xenopus laevis*, reticulocyte lysates or wheat germs to be translated thereby into the protein, and the resulting protein is checked to see whether or not it has a cytotoxic activity against mouse L-P3 cells. More precisely, the method for the confirmation by the use of oocytes of *Xenopus laevis* is carried out, for example, as follows:

The mRNA is injected into the oocytes in an amount of about 50 to 100 ng per oocyte by a micro-injection method, and 20 oocytes are incubated in 200 μl of a modified Barth salt solution (containing 0.13 g of NaCl, 0.075 g of KCl, 0.2 g of NaHCO$_3$, 0.2 g of MgSO$_4$7H$_2$O, 0.08 g of Ca(NO$_3$)$_2$.4H$_2$O, 0.09 g of CaCl$_2$.6H$_2$O, 2.38 g of HEPES, 100 mg of streptomycin and 100,000 units of penicillin G dissolved in 1 liter of the solution at a pH of 7.4, which solution is hereinafter referred to as MBS) at 23° C. for 48 hours. The supernatant liquid of the cultured solution is used as a sample, and the LT-activity of the sample is measured on the basis of the index of the L-P3 cytotoxic activity.

The LT-encoding mRNA of the present invention has the following characteristics:

(i) it has an S-value of 12.6S to 14.6S;
(ii) it has a polyadenylic acid structure at the 3'-terminal;
(iii) it encodes an LT-polypeptide.

(6) Cloning of lymphotoxin-cDNA:

The mRNA obtained in step (5) above is used as a template and oligo(dT) is used as a primer, and a single-stranded cDNA which is complementary to the mRNA is synthesized with a reverse transcriptase (such as avian myeloblastosis virus-derived reverse transcriptase) in the presence of dATP, dGTP, dCTP and dTTP, and the template mRNA is denaturated by heat-treatment. Next, this single-stranded cDNA is used as a template and a double-stranded DNA is synthesized by the use of DNA polymerase I (Klenow fragment) derived from *Escherichia coli*. This double-stranded DNA is isolated from the denatured mRNA and protein by alkali-treatment and phenol-extraction. This double-stranded DNA is reacted with the reverse transcriptase thereby to obtain a more complete double-stranded DNA. The thus obtained DNA has a hair-pin loop structure, and the hair-pin loop structure is cleaved by the use of S$_1$-nuclease (*Aspergillus oryzae*-derived S$_1$ nuclease), to obtain a DNA with a complete double-stranded structure. The DNA thus obtained is inserted, for example, into the restriction enzyme PstI-cleaved site of plasmid pBR322 in a conventional manner such as poly(dG)-poly(dC)- or poly(dA)-poly(dT)-homopolymer extension method (Noda, M. et al., Nature, 295, 202 1982); Maniatis, T. et al., Molecular Cloning (a laboratory manual), 217 (1982), Cold Spring Harbor Laboratory, New York). The resulting recombinant plasmid is introduced into a host such as *E. coli* HB101 strain for the transformation, in accordance with the method by Perbal, B. (A Practical Guide to Molecular Cloning, 268 (1984), John Wiley & Sons Inc., Canada), a tetracycline-resistant strain is selected and a cDNA library is formed.

The cDNA library is subjected to the colony-hybridization test utilizing a synthetic probe (Montgomery, D. L. et al., Cell, 14, 673 (1978); Goeddel, D. V. et al., Nucleic Acids Res., 8, 4057 (1980)), to screen for the desired clone. For instance, two oligonucleotides are chemically synthesized, which corresponds to 18 bases from the 404th to 421st nucleotides and complementary 18 bases from the 500th to 517th nucleotides in the lymphotoxin gene as reported by Gray, et al. in Nature, 312, 721 (1984), and γ-phosphate of γ-$^{32}$P-ATP is transferred to the hydroxyl group in the 5'-terminal of the probe with a polynucleotide kinase (T4 phage-infected *E. coli*-derived T4 polynucleotide kinase), so that two kinds of $^{32}$P-labeled probes are formed. From the above-mentioned cDNA library is selected a clone capable of strongly binding with both probes. Plasmid DNA is isolated from the thus obtained clone, and this is changed into a single-stranded DNA by heating or alkali-denaturation, which is fixed on a nitrocellulose filter. To this is added a lymphotoxin mRNA-containing mRNA-fraction for hybridization, and then the bound mRNA is recovered by elution. This is injected into oocytes of *Xenopus laevis*, and the recovered mRNA is checked as to whether or not it encodes lymphotoxin. (This is hereinafter referred to as "hybridization-translation test".) According to the above-mentioned method, a cloned DNA into which has been inserted a DNA fragment containing a base sequence which is complementary with the mRNA of lymphotoxin can be obtained.

In addition, the cloned DNA fragment of the transformant strain is cleaved with pertinent restriction enzymes and labeled with $^{32}$P, and this is used as a probe for re-screening the above-mentioned cDNA library so that a cDNA fragment of a larger size can be selected.

A restriction endonuclease cleavage map of the cloned DNA fragment thus obtained is formed, the fragment is cloned with M13-phage, the base sequence thereof is analyzed in accordance with the dideoxy-sequence method by Sanger F. et al. (Proc. Natl. Acad. Sci. USA, 5463 (1977)), the nucleotide sequence encoding the amino acid sequence of the lymphotoxin which has already been determined is traced, and finally, the cDNA containing the nucleotide sequence (that is, the nucleotide sequence from the 165th to 677th nucleotides in the above-mentioned Table 1) which corresponds to the complete translation range of lymphotoxin is selected out, whereby the cloned DNA (Table 1) having the nucleotide sequence encoding the polypeptide containing the LT amino acid sequence can be obtained.

The plasmid pBR322 into which has been inserted the cloned DNA which encodes the polypeptide containing LT amino acid sequence as shown in the Table 1 was called pLT13. *E. coli* HB101 strain was transfected with the pLT13 to obtain a recombinant strain, and this was deposited in Fermentation Research Institute (Bikoken), Agency of Industrial Science and Technology, Ministry of International Trade and Industry, Japan under deposit number FERM-BP No. 1226 on Nov. 29, 1986 under the Budapest Treaty.

The cDNA as shown in Table 1, which is obtained by the present invention, differs from the known LT gene as shown in the above-mentioned Table 2, and it was not clear initially whether or not the product of the cDNA of the present invention (as shown in the Table 1) had LT-activity. This is because a difference of only one amino acid between proteins can result in an extreme difference in the properties between the two proteins.

Accordingly, the present inventors made another trial, where the pLT13 is cleaved with pertinent restriction enzymes, the cleaved fragment is inserted into a phenotypic expressing vector and the resulting plasmid is introduced into *E. coli* or animal cells for the transfection, and these are checked as to whether or not they can express LT activity. As a result, both the transfected bacteria and animal cells were confirmed to express LT activity, and thus, it is concluded that the cDNA shown in Table 1 actually is the cDNA encoding the amino acid sequence of LT, as mentioned in the following (7) and in the working examples to follow.

(7) Preparation of Phenotypic Expressing Vector which Contains the Nucleotide Sequence Encoding LT(I)

(a) Cleavage of cDNA encoding the amino acid sequence of LT-polypeptide with restriction enzymes:

For the preparation of DNA encoding the amino acid sequence of the present invention, the complete cDNA as shown in Table 1 is cleaved with restriction enzymes PvuII and EcoRI in a conventional manner fractionated by agarose/gel electrophoresis to extract the cDNA fragment comprising about 650 base pairs (hereinafter abbreviated as "bp"), and the cDNA fragment is recovered. This cDNA fragment contains the 193rd to 840th bases in the complete cDNA as shown in Table 1.

(b) Cleavage of the polylinker site of phenotypic expressing vector with restriction enzymes:

The polylinker site of phenotypic expressing vector pKK223-3 (by Pharmacia Co.) is first completely cleaved with EcoRI and then partially cleaved with BamHI, and both the vector which is partially cleaved with the BamHI and the vector which is not cleaved with the BamHI are recovered by agarose gel electrophoresis. In addition, the mixed vectors are completely cleaved with SmaI. Thus, the vector in which the cleaved site is an EcoRI-BamHI site and the vector in which the cleaved site is an EcoRI-SmaI site are formed.

(c) Ligation of translation-initiating site and EcoRI-BamHI site-cleaved pKK223-3:

The EcoRI-BamHI site-cleaved vector of pKK223-3 and a portable translation-initiating site having the following structure (which is formed by annealing a terminal EcoRI site-containing top chain and a terminal BamHI site-containing bottom chain, both chains being commercial products by Pharmacia Co.) are reacted in the presence of T4 DNA ligase, to again obtain a vector having a circular structure.

AATTTGGAGGAAAAAATTATG
ACCTCCTTTTTTAATACCTAG

The thus re-formed vector is introduced into E. coli for transformation, and the strain containing the re-formed vector is selected as an ampicillin-resistant strain, and the re-formed vector is recovered from the cultured bacteria.

(d) Insertion of the LT cDNA fragment formed in (a) into the re-formed vector prepared in (c):

The re-formed vector prepared in the (c) above is partially cleaved with BamHI and then the 5'-terminal thereof is dephosphorylated with bovine intestine mucosa-derived alkaline phosphatase, and further, the cohesive end is converted to a blunt end with DNA polymerase I (Klenow fragment). On the other hand, the PvuII-EcoRI cleaved site of the LT-cDNA as formed in (a) above is modified to have a blunt end and this is subjected to blunt end ligation with the above-mentioned blunt end-containing open circular vector. After the reaction, the closed circular vector is recovered in a conventional manner and it is introduced into E. coli for transformation.

(e) Screening with a synthetic oligonucleotide probe:

The $^{32}$P-labeled synthetic oligonucleotide probe shown in (6) above and the transformant E. coli strain formed in (d) above are subjected to colony hybridization, and the strain capable of being hybridized with the synthetic oligonucleotide probe is selected. Next, a vector is prepared from the colony and cleaved with restriction enzymes, and thus, the desired vector containing cDNA fragments of about 650 bp and about 250 bp is obtained by agarose-gel electrophoresis.

(8) Production of LT(I) in E. coli

The transformant E. coli obtained in (e) above are incubated in a medium containing isopropyl-$\beta$-D-thiogalactopyranoside (hereinafter referred to as IPTG) until the O.D. 550 nm reaches about 1.

After the incubated bacteria are collected, they are lysed by ultrasonic wave-treatment, extracted with Tris-HCl buffer (pH 8.0) and filtered under germ-free conditions, and then, the LT-activity is measured whereby the transformant strain which expresses the largest amount of LT-polypeptide is screened.

(9) Incubation and Purification of LT(I)-producing E. coli

The transformants (LT-producing E. coli) obtained in (8) above are incubated in an IPTG-containing medium until a sufficient amount of the LT-polypeptide is produced. Next, the incubated material is disintegrated by a method such as lysozyme-digestion, freezing and thawing method, ultrasonic disintegration, French press, Dinor mill, etc., and the extract solution is collected by centrifugation or filtration. The resulting extract solution is purified by a combination of ammonium sulfate salting-out, ultra-filtration, ion exchange-chromatography, hydrophobic chromatography, gel-filtration and SDS polyacrylamide gel electrophoresis, whereby LT-polypeptide can be obtained in the form of a substantially pure product.

(10) The LT(I) as obtained in (9) above was analyzed to determine the amino acid composition and the N-terminal amino acid sequence, and as a result, the values measured by the analysis were the same as those as assumed from the amino acid sequence (I), as shown in the working example to follow. The isoelectric point was 7.6±0.3.

The DNA encoding amino acid sequence (I) and its corresponding the base nucleotide sequence (I) are shown hereinbelow:

Amino acid sequence (I):
MET ASP PRO ALA GLN THR ALA ARG GLN HIS
PRO LYS MET HIS LEU ALA HIS SER ASN LEU
LYS PRO ALA ALA HIS LEU ILE GLY ASP PRO
SER LYS GLN ASN SER LEU LEU TRP ARG ALA
ASN THR ASP ARG ALA PHE LEU GLN ASP GLY
PHE SER LEU SER ASN ASN SER LEU LEU VAL
PRO THR SER GLY ILE TYR PHE VAL TYR SER
GLN VAL VAL PHE SER GLY LYS ALA TYR SER
PRO LYS ALA THR SER SER PRO LEU TYR LEU
ALA HIS GLU VAL GLN LEU PHE SER SER GLN
TYR PRO PHE HIS VAL PRO LEU LEU SER SER
GLN LYS MET VAL THR PRO GLY LEU GLN GLU
PRO TRP LEU HIS SER MET TYR HIS GLY ALA
ALA PHE GLN LEU THR GLN GLY ASP GLN LEU
SER THR HIS THR ASP GLY ILE PRO HIS LEU
VAL LEU SER PRO SER THR VAL PHE PHE GLY
ALA PHE ALA LEU nucelotide sequence (I):
ATG GAT CCT GCC CAG ACT GCC CGT -continued
```
CAG CAC CCC AAG ATG CAT CTT GCC CAC AGC
AAC CTC AAA CCT GCT GCT CAC CTC ATT GGA
GAC CCC AGC AAG CAG AAC TCA CTG CTC TGG
AGA GCA AAC ACG GAC CGT GCC TTC CTC CAG
GAT GGT TTC TCC TTG AGC AAC AAT TCT CTC
CTG GTC CCC ACC AGT GGC ATC TAC TTC GTC
TAC TCC CAG GTG GTC TTC TCT GGG AAA GCC
TAC TCT CCC AAG GCC ACC TCC TCC CCA CTC
TAC CTG GCC CAT GAG GTC CAG CTC TCC TCC
TCC CAG TAC CCC TTC CAT GTG CCT CTC CTC
AGC TCC CAG AAG ATG GTG TAT CCA GGG CTG
CAG GAA CCC TGG CTG CAC TCG ATG TAC CAC
GGG GCT GCG TTC CAG CTC ACC CAG GGA GAC
CAG CTA TCC ACC CAC ACA GAT GGC ATC CCC
CAC CTA GTC CTC AGC CCT AGT ACT GTC TTC
TTT GGA GCC TTC GCT GCT-(3'-)
```

(11) The LT(I) of the present invention was stable to pH variation, and even when incubated in a Britton-Robinson buffer solution in a broad range of pH's of 4–10 for 24 hours, the LT-activity persisted.

(12) Preparation of phenotypic expressing vector which contains the nucleotide sequence to encode LT(II):

(a) Cleavage of cDNA to encode LT(II) with restriction enzymes:

For the preparation of DNA to encode the amino acid sequence of the present invention, the complete cDNA as shown in the Table 1 is cleaved with restriction enzymes PvuII and EcoRI in a conventional manner and fractionated by agarose-gel electrophoresis to extract the cDNA fragment comprising about 650 base pairs (bp), and the cDNA fragment is recovered. This cDNA fragment contains the 225th to 840th bases in the complete cDNA as shown in Table 1.

(b) Ligation of synthetic oligonucleotide and LT-cDNA fragment:

The synthetic oligonucleotide having the following structure:

AATTCTATGCA
GAT and the LT-cDNA fragment obtained in (a) above are ligated and then digested with EcoRI and the EcoRI fragment of 623 bp is recovered in a conventional manner.

(c) Insertion of the LT-cDNA into expressing vector:

Expressing vector pKK223-3 (obtained from Pharmacia Co.) is digested with EcoRI and then the 5'-terminal is dephosphorylated with bovine intestine mucosa-derived alkaline phosphatase. The EcoRI fragment obtained in (b) above and the above-mentioned open circular vector are ligated. After the reaction, the closed circular vector is recovered in a conventional manner, and this is inserted into *E. coli* for transformation.

(d) Screening by a synthetic oligonucleotide probe:

The $^{32}P$-labeled synthetic oligonucleocide probe shown in (6) above and the transformant *E. coli* strain formed in (c) above are subjected to colony hybridization, and the strain capable of being hybridized with the synthetic oligonucleotide probe is selected. Next, a vector is prepared from the colony and cleaved with restriction enzymes, and thus, the desired vector containing a cDNA fragment of 623 bp is obtained by agarose-gel electrophoresis.

(13) Preparation of Vector where the 3'-terminal Non-coding Region of LT-cDNA has been Removed (a) Removal of 3'-terminal non-coding region of LT-cDNA:

The vector obtained in (12) above is converted into a linear DNA by the use of HindIII, and then the 3'-terminal non-coding region of LT-cDNA is removed with BAL31-nuclease. Next, the terminal is made blunt with DNA-polymerase-1 (Klenow fragment) and then the vector is digested with EcoRI and thereafter fractionated by polyacrylamide gel electrophoresis to recover a fragment of about 460 bp.

(b) Ligation of LT-cDNA and linker:

The 460 bp fragment obtained in (a) above and a HindIII-linker (made by Takara Shuzo Co.) are ligated and then digested with HindIII.

(c) Ligation of LT-cDNA and expressing vector:

pKK223-3 is digested with EcoRI and HindIII to obtain a fragment of 4555 bp. Next, the EcoRI-HindIII fragment of about 465 bp obtained in (b) above is linked with the fragment, and the resulting fragment is inserted into E. coli for transformation in a conventional manner, co obtain a vector having LT-cDNA fragment of about 465 bp.

(14) Formation of Multiple Copy-expressing Vector pAT153 (made by Amersham Co.) is digested with BamHI and PvuI and fractionated by agarose-gel electrophoresis, to obtain a fragment of 2655 bp. On the other hand, the vector as obtained in (13) above is also digested with BamHI and PvuI to obtain a fragment of about 980 bp, analogously. These two BamHI-PvuI fragments are ligated, to obtain a vector having an LT-cDNA fragment.

(15) Expression of LT-cDNA in *E. coli*

The transformant *E. coli* obtained in (14) above are incubated in a medium containing IPTG until the O.D. 550 nm reaches about 1.

After the incubated bacteria are collected, these are disintegrated by ultrasonic wave-treatment, extracted with Tris-HCl buffer (pH 8.0) and filtered under germ-free conditions, and then, the LT-activity is measured whereby the transformant strain which expresses the largest amount of LT-polypeptide is screened.

(16) Incubation and Purification of LT-polypeptide-producing *E. coli*

The transformant (LT-producing *E. coli*) obtained in (14) above are incubated in an IPTG-containing medium until a sufficient amount of LT-polypeptide is produced. Next, the incubated material is disintegrated by a method such as lysozyme-digestion, freezing and thawing method, ultrasonic disintegration, French press, Dinor mill, etc., and the extract solution is collected by centrifugation or filtration. The resulting extract solution is purified by a combination of ammonium sulfate salting-out, ultra-filtration, ion exchange-chromatography, hydrophobic chromatography, gel-filtration and SDS-polyacrylamide gel electrophoresis, whereby LT-polypeptide can be obtained in the form of a substantially pure product.

(17) The LT(II) as obtained in (16) above was analyzed to determine the amino acid composition and the N-terminal amino acid sequence, and as a result, the values measured by the analysis were same as those assumed from the amino acid sequence (II), as shown in the working example to follow.

The DNA encoding the amino acid sequence (II) and its corresponding nucleotide sequence (II) are shown hereinbelow:

Amino acid sequence (II)

MET HIS LEU ALA HIS SER ASN LEU LYS PRO
ALA ALA HIS LEU ILE GLY ASP PRO SER LYS
GLN ASN SER LEU LEU TRP ARG ALA ASN THR
ASP ARG ALA PHE LEU GLN ASP GLY PHE SER
LEU SER ASN ASN SER LEU LEU VAL PRO THR
SER GLY ILE TYR PHE VAL TYR SER GLN VAL
VAL PHE SER GLY LYS ALA TYR SER PRO LYS
ALA THR SER SER PRO LEU TYR LEU ALA HIS
GLU VAL GLN LEU PHE SER SER GLN TYR PRO
PHE HIS VAL PRO LEU LEU SER SER GLN LYS
MET VAL TYR PRO GLY LEU LEU GLN PRO TRP
LEU HIS SER MET TYR HIS GLY ALA ALA PHE
GLN LEU THR GLN GLY ASP GLN LEU SER THR
HIS THR ASP GLY ILE PRO HIS LEU VAL LEU
SER PRO SER THR VAL PHE PHE GLY ALA PHE
ALA LEU

Nucleotide sequence (II)

(5')-ATG CAT CTT GCC CAC AGC
AAC CTC AAA CCT GCT GCT CAC CTC ATT GGA
GAC CCC AGC AAG CAG AAC TCA CTG CTC TGG
AGA GCA AAC ACG GAC CGT GCC TTC CTC CAG
GAT GGT TTC TCC TTG AGC AAC AAT TCT CTC
CTG GTC CCC ACC AGT GGC ATC TAC TTC GTC
TAC TCC CAG GTG GTC TTC TCT GGG AAA GCC
TAC TCT CCC AAG GCC ACC TCC TCC CCA CTC
TAC CTG GCC CAT GAG GTC CAG CTC TTC TCC
TCC CAG TAC CCC TTC CAT GTG CCT CTC CTC
AGC TCC CAG AAG ATG GTG TAT CCA GGG CTG
CAG GAA CCC TGG CTG CAC TCG ATG TAC CAC
GGG GCT GCG TTC CAG CTC ACC CAG GGA GAC
CAG CTA TCC ACC CAC ACA GAT GGC ATC CCC
CAC CTA GTC CTC AGC CCT AGT ACT GTC TTC
TTT GGA GCC TTC GCT CTG-(3'-)

(18) Preparation of Phenotypic Expression Vector which Contains Gene Encoding Amino Acid Sequence of LT (III)

For causing expression of the gene coding for the amino acid sequence of the LT polypeptide shown in sequence (III) in a microorganism, for example *Escherichia coli*, it is necessary to insert the LT cDNA gene, together with the initiation codon (ATG) added thereto, downstream from a pertinent promoter such as the tac (trc) promoter or trp promoter. A ribosome binding site is also required 5 to 15 bases upstream from the initiation codon.

Generally, when a mammalian gene is caused to be expressed in a microorganism, for example, *Escherichia coli*, the yield is sometimes low. Presumably, the causes are concerned with, for example (1) the transcription efficiency of the promoter, (2) the nucleotide sequence and secondary structure of the ribosome binding site and the vicinity of ATG, (3) the codon frequencies and (4) degradation of the product. As far as point (I) is concerned, the tac (lac series) promoter or trp promoter is in general use. As regards point (2), an optimum one should be searched for among various ribosome binding sites. As for point (3), mammals differ in codon frequencies from *Escherichia coli* and, therefore, changes no codons used in *Escherichia coli* are desirable in some instances. Regarding point (4), introduction into various strains of *Escherichia coli* and/or incorporation, for more complete control, of a repressor gene into the expression vector is important. It is also important to substitute or delete those bases that correspond to amino acid residues readily cleavable with proteases. It is an effective means as well to fuse the nucleotide sequence corresponding to the signal peptide with the LT cDNA so that the expression product can be secreted into the periplasm or culture medium.

In practicing the invention, it is recommended that the LT expression vector should be constructed while paying particular attention to points (1), (3) and (4). Thus, trc (a kind of tac promoter) is employed, and the synthetic DNA portion corresponding to the N terminus of LT is modified, for facilitating the subsequent gene manipulation procedure, such that it contains those codons that are best suited for *Escherichia coli* except for restriction enzyme recognition site introduction. Furthermore, for host screening and for efficient induction, a repressor gene is introduced into the expression vector.

For expression of cDNA encoding LT polypeptide according to the present invention, the known strain of *Escherichia coli* such as HB101 (Bethesda Research Laboratories), JM105 (Pharmacia) W3110 (ATCC 27325) and Y1089 (ATCC 37196) can be used as a host. The strain W3110 can be preferably used due to high LT-productivity.

The medium for use in cultivating *Escherichia coli* transformants harboring the LT expression vector constructed in the above-mentioned manner may be a natural medium or a synthetic medium.

As far as the cultivation conditions are concerned, it is necessary to search for each of the incubation temperature, pH, rate of stirring and rate of aeration which are suited for LT production.

(19) Cultivation of LT Polypeptide-producing *Escherichia coli* and Purification of LT Polypeptide The transformant (LT-producing *Escherichia coli*) obtained in step (18) is cultivated in an IPTG-containing medium until a sufficient amount of the LT polypeptide is produced. The incubated material is then disintegrated by sonication, by means of an APV Gaulin high-pressure homogenizer, or by a similar means, and the disintegrated matter or the supernatant obtained by centrifugation of the same is subjected to a combination of salting out with ammonium sulfate, ultrafiltration, ion exchange chromatography, gel filtration, heat treatment, reversed phase chromatography and chelete resin chromatography, whereby the LT polypeptide can be obtained as a substantially pure product.

The LT polypeptide obtained in step (18) was analyzed for amino acid composition and N-terminal amino acid sequence. The data obtained were in agreement with the values estimated from sequence (III), as shown in the relevant working example.

The DNA nucleotide sequence coding for the amino acid sequence (III) and its corresponding nucleotide sequence (III) is shown below.

Amino acid sequence (III)

1 10
MET HIS LEU ALA SER ASN LEU LYS PRO ALA
20
ALA HIS LEU ILE GLY ASP PRO SER LYS GLN
30
ASN SER LEU LEU TRP ARG ALA ASN THR ASP
40
ARG ALA PHE LEU GLN ASP GLY PHE SER LEU
50
SER ASN ASN SER LEU LEU VAL PRO THR SER
60
GLY ILE TYR PHE VAL TYR SER GLN VAL VAL
70
PHE SER GLY LYS ALA TYR SER PRO LYS ALA

-continued

```
                                        80
THR SER SER PRO LEU TYR LEU ALA HIS GLU
                                        90
VAL GLN LEU PHE SER SER GLN TYR PRO PHE
                                        100
HIS VAL PRO LEU LEU SER SER GLN LYS MET
                                        110
VAL TYR PRO GLY LEU GLN GLU PRO TRP LEU
                                        120
HIS SER MET TYR HIS GLY ALA ALA PHE GLN
                                        130
LEU THR GLN GLY ASP GLN LEU SER THR HIS
                                        140
THR ASP GLY ILE PRO HIS LEU VAL LEU SER
                                        150
PRO SER THR VAL PHE PHE GLY ALA PHE ALA

LEU
``` nucleotide sequence (III)

```
       (5')-ATG CAT CTG GCT TCT
AAC CTG AAA CCC GCG GCT CAC CTG ATC GGT
GAC CCG TCT AAA CAG AAC TCT CTG CTG TGG
CGT GCT AAC ACG GAC CGT GCC TTC CTC CAG
GAT GGT TTC TCC TTG AGC AAC AAT TCT CTC
CTG GTC CCC ACC AGT GGC ATC TAC TTC GTC
TAC TCC CAG GTG GTC TTC TCT GGG AAA GCC
TAC TCT CCC AAG GCC ACC TCC TCC CCA CTC
TAC CTG GCC CAT GAG GTC CAG CTC TTC TCC
TCC CAG TAC CCC TTC CAT GTG CCT CTC CTC
AGC TCC CAC AAG ATG GTG TAT CCA GGG CTG
CAG GAA CCC TGG CTG CAC TCG ATG TAC CAC
GGG GCT GCG TTC CAG CTC ACC CAG GGA GAC
CAG CTA TCC ACC CAC ACA GAT GGC ATC CCC
CAC CTA GTC CTC AGC CCT AGT ACT GTC TTC
TTT GGAGCC TTC GCT CTG-(3'-)
```

(20) Antitumor Activity of LT Polypeptide

It has been revealed that the LT polypeptide according to the present invention is cytocidal to animal tumor cells in vitro and in vivo and can be used as an antitumor agent. An antitumor composition according to the present invention comprises a tumor treating effective amount of the LT polypeptide and a pharmaceutically acceptable carrier. The antitumor composition of the present invention can be prepared by mixing the LT polypeptide with a pharmaceutically acceptable stabilizer such as gelatin, serum albumin or maltitol and an appropriate excipient, if desired. The dosage varies dependent on the route of administration, the kind of cancer and the body weight of the patient. The nontoxic amount of the LT polypeptide for a mouse is $1 \times 10^3$ to $5 \times 10^7$ units/kg/day in the case of intravenous injection (i.v.) or intratumoral injection (i.t.).

The present invention will be explained in greater detail by reference to the following examples, which, however, are not intended to be interpreted as limiting the scope of the present invention.

EXAMPLE 1

(1) Preparation of Lymphotoxin-Producing Human T-Cell Hybridoma $10^6$/ml of human peripheral blood lymphocytes (hereinafter referred to as PBL) were treated with 20 $\mu$g/ml of Con A in RPMI-medium for 2 days, and then, the Con A as bonded with the cells was removed as much as possible by the use of 0.2M of $\alpha$-methyl-D-mannoside.

On the other hand, human T-lymphoid tumor cells CCRF-CEM (hereinafter referred to as CEM) which were in a growing stage in RPMI-medium were collected by centrifugation, and these were suspended in RPMI 1640/10 mM-HEPES medium in an amount of $2 \times 10^6$ cells/ml. To this were added emetine hydrochloride (made by Nakarai Chemical Co.) and actinomycin-D (made by PL Biochemicals Co.) in an amount of $5 \times 10^{-5}$M and 0.25 $\mu$g/ml, respectively, and this was treated at 37° C. for 2 hours. Then, the emetine hydrochloride and acitnomycin D in the cultured solution were removed by centrifugation.

PBL and CEM thus prepared were mixed in a ratio of 10:1 and centrifuged to obtain cell pellets, and to this were added 0.5 ml of 46% polyethylene glycol (PEG-1540, made by Wako Junyaku KK) and MEM-medium containing 5 $\mu$g/ml of poly-L-arginine and 15%-dimethylsulfoxide and slowly stirred for 45 seconds at 37° C. for hybridization. Thereafter, 10ml of MEM-medium buffered with HEPES (25 mM, pH 7.2) was gradually added thereto and the mixture was centrifuged.

RPMI-medium was added to the cell pellets, and the cell number was regulated to be $10^6$/ml. 100 $\mu$l of the resulting cell-containing medium was mixed with 100 $\mu$l of RPMI-medium containing mitomycin C-treated CEM ($4 \times 10^5$ cells/ml) as feeder cells, and the resulting mixture was put in 96-well culture plate and incubated at 37° C. under an atmosphere of $CO_2$(5%)-air(95%) for about 3 to 4 weeks. After the incubation, the grown hybridoma cells were cloned by limiting dilution-culture method using the above-mentioned mitomycin C-treated CEM as feeder cells. After the growth of each clone, the lymphotoxin-activity was measured.

The incubation hereinafter was carried out under an atmosphere of $CO_2$(5%)-air(95%) at 37° C., unless otherwise specifically indicated.

The lymphotoxin-producing cloned human T-cell hybridoma A-C5-8 strain of the present invention, which was in the form of a solution of a cell concentration of $2.5 \times 10^5$ cells/ml, was stimulated with 20 $\mu$g/ml of of Con A and 20 ng/ml of PMA and incubated for 24 hours, and as a result, the lymphotoxin-activity was 250 units/ml. On the other hand, the nonstimulated A-C5-8 strain had a lymphotoxin-activity of 4 units/ml.

EXAMPLE 2

Isolation and Purification of mRNA Fraction From Lymphotoxin-Producing Human T-Cell Hybridoma (A-C5-8)

(1) Incubation of Lymphotoxin-Producing Human T-Cell Hybridoma (A-C5-8)

A-C5-8 cell line, which was in the form of a suspension having a cell concentration of $5 \times 10^6$ to $10^7$/ml, was incubated for 2, 4, 8, 24 and 48 hours, while PMA and Con-A were added thereto in a final concentration of 100 ng/ml and 20 $\mu$g/ml, respectively, (2) Preparation of Total Cellular RNA The extraction of the total cellular RNA of the A-C5-8 cell line was essentially carried out by the guanidine hydrochloride method. More precisely, after incubating the A-C5-8 cell line for the same time periods as in (1) above, the cells were collected by centrifugation (1000 rpm, 5 minutes) and were suspended in PBS (containing 5 mM of phosphate buffer and 0.15M of NaCl and having pH of 7.4), and the resulting suspension was further centrifuged for 5 minutes at 1000 rpm and the collected cells were washed.

The cells (in an amount of $4 \times 10^8$, $6 \times 10^8$, $3.2 \times 10^8$, $1.8 \times 10^9$ and $2 \times 10^9$ in each incubation period in step (1), respectively) were suspended in a homogenate-buffer (containing 8M of guanidine hydrochloride, 5 mM of dithiothreitol and 20 mM sodium acetate and having pH 7.0) and homogenized therein. To the resulting homogenate were added 0.025 equivalent of 1M-acetic acid and 1.5 times the amount of cold ethanol (at −20° C.) and the mixture was blended. Then, the resulting mixture was kept at −20° C. for 3 hours or more. Next, this was centrifuged at −10° C. for 30 minutes at 15000 rpm by the use of Hitachi's RPR 18-2 Rotor. To the resulting precipitate was added a washing buffer (made by adding 20 mM of EDTA.2Na to the homogenate-buffer, which is hereinafter referred to as WB) and uniformly dissolved by pipetting. Then, 1M of acetic acid was added thereto to regulate the pH value thereof to 5, and thereafter, 1.5 times the amount of cold ethanol was added thereto and the whole was kept at −20° C. for 3 hours or more. This was centrifuged at −10° C. for 30 minutes at 15000 rpm, the resulting precipitate was dissolved in WB. The pH regulation with 1M-acetic acid and the cold ethanol-precipitation were repeated three times.

A small amount of 0.1%-SDS was added to the ethanol-precipitate to make a suspension, and to this were added one equivalent of an extraction-buffer (containing 0.5% of SDS, 0.1M of NaCl, 50 mM of sodium acetate and 5 mM of $EDTA_{2Na}$ and having pH of 5.2) and two equivalents of water-saturated phenol (containing 0.1%-8-quinolinol and saturated with 100 mM-Tris-HCl buffer of pH 8.0)/chloroform/isoamyl alcohol solution (volume ratio of 50:50:1). The mixture was shaken for 10 minutes, and then the resulting mixture was centrifuged for 10 minutes at 3000 rpm. After the centrifugation, the mixture was divided into three layers, and the lowest layer was removed. The equivalent amount of chloroform/isoamyl alcohol solution (volume ratio of 50:1) was added to each of the top layer and the middle layer and the mixture was shaken for 10 minutes, and then, the resulting mixture was centrifuged for 10 minutes at 3000 rpm and the lowest layer was removed. The extraction with the chloroform/isoamyl alcohol solution was repeated three times. 0.1 equivalent amount of 3M-sodium acetate (pH 5.2) was added to the upper layer containing DNA, RNA and saccharides, and then, two equivalents of cold ethanol was added thereto and the whole was kept at −20° C. for 3 hours or more and thereafter centrifuged for 30 minutes at 15000 rpm (RPR 18-2 Rotor). A small amount of germ-free distilled water was added to the resulting precipitate and dissolved, and then, the equivalent amount of cold 4M-lithium chloride was added thereto and kept at 0° C. for one night. Thereafter, the mixture was centrifuged for 30 minutes at 15000 rpm. The resulting precipitate was washed with a small amount of 2M-lithium chloride, and then, a germ-free distilled water was added thereto and dissolved, and, after 1/10 equivalent amount of 3M-sodium acetate (pH 5.2) was added thereto, two equivalents of cold ethanol was added thereto, and the whole was kept at −20° C. for 3 hours or more. This was centrifuged for 30 minutes at 15000 rpm, and the resulting precipitate was dissolved in 0.01M of Tris-HCl buffer (containing 0.5M of NaCl, 0.1% of SDS and 1 mM of $EDTA_{3Na}$ and having a pH of 7.5). Next, 3 ml of oligo(dT)$_{12-18}$-cellulose (made by PL Biochemicals Co.) which had previously been buffered with the same buffer was filled in a column having a diameter of 1 cm, and the total cellular RNA fraction was fed into the column. This was washed with the same buffer until the absorbance of 260 nm reached 0.05 or less, and then, elution with 0.01M of Tris-HCl buffer (containing 0.5M of NaCl, 0.1% of SDS and 1 mM of $EDTA_{3Na}$ and having pH of 7.5) was begun and the column was washed until the absorbance at 260 nm reached 0.05 or less. In the end, 0.01M of Tris-HCl buffer (containing 0.1% of SDS and 1 mM of EDTA.3Na and having pH of 7.5) was passed through the column for elution to dissolve the polyadenylic acid-bonded RNA (mRNA) therefrom, which was collected with a fraction collector, and the fraction having a detectable absorbance of 260 nm was collected. Thus, 58 μg, 130 μg, 180 μg, 120 μg and 258 μg of mRNA were recovered from the A-C5-8 cells as incubated for 2, 4, 8, 24 and 48 hours, respectively.

(3) Confirmation of the Translation of LT-corresponding mRNA in Oocytes

A pregnant mare's serum gonadotropin (veterinary Peamex injection, by Sankyo Co.) was injected into *Xenopus laevis* of about 2 years (female, weight: 50 g or more, commercial products by Japan Biological Material Center), in the thigh by intramuscular injection, in an amount of 200U/animal. The next day, the animals were anesthetized by dipping in ice-water, whereupon the abdomen was dissected and oocytes were taken out and these were isolated in MBS. The mRNA obtained in step (2) above was dissolved in germ-free distilled water to form a solution of 1 mg/ml, and the resulting solution was injected into the oocytes having a diameter of 1 mm or more in an amount of 50 nl (50 ng) per oocyte by the use of a microcapillary and a microinjector (made by Narishige Scientific Instruments Co.) under observation with a practical microscope. 20 oocytes thus treated were incubated in 0.2 ml of MBS at 23° C. For a control test, 20 oocytes treated with only 50 nl of a germ-free distilled water were analogously incubated in 0.2 ml of MBS at 23° C.

After incubation for 24 hours or 48 hours, the LT-activity of the supernatant liquid of the culture solution was measured, and as a result, it was confirmed that incubation for 48 hours is the optimum condition for the incubation of the oocytes. Regarding the incubation time of the A-C5-8 cells as stimulated with Con-A and PMA, the LT-activity as translated from the mRNA in the cells incubated for 2, 4, 8, 24 and 48 hours was 7.8, 4.6, 4.1, 2.7 and 0 unit/ml, respectively, and therefore, the best incubation time of the A-C5-8 cells for obtaining mRNA was found to be 2 hours. No LT-activity was detected in the corresponding control test, and therefore, it was confirmed that the mRNA of LT was translated in the oocytes.

(4) Mass-incubation of A-C5-8 Cells and Production of mRNA

The A-C5-8 cells were incubated under the best condition (under stimulation with Con A and PMA) as determined in the above step (3) and $3 \times 10^9$ cells were collected. The mRNA was isolated and purified from these cells in accordance with step (2) above, to obtain 512 μg of the mRNA fraction.

(5) Fractionation of mRNA by Sucrose Density-gradient Centrifugation Method and Determination of LT-corresponding mRNA Sedimentation Coefficient 512 μg of the mRNA as obtained in the above step (4); was dissolved in 0.01M of Tris-HCl buffer (containing 0.01M of $EDTA_{2Na}$ and 0.2% of SDS and having pH of 7.5), and this was put over 5 ml of 5 to 30%-sucrose density-gradient solution as dissolved in the same buffer and then centrifuged for 16 hours at 15° C. at 28000 rpm by the use of RPR 55T-Rotor (by Hitachi Co.). Next, the content was fractionated into 25 vials (each having a capacity of 216 μl). 1/10 equivalent of 3M-sodium acetate and two equivalents of cold ethanol were added to each fraction and kept at −20° C. for one night, to thereby recover mRNA.

The mRNA thus recovered was dissolved in germ-free distilled water (0.5 mg/ml), and 100 nl of the resulting solution was injected into 20 oocytes in the same manner as step (3) above. The oocytes were incubated for 48 hours with 0.2 ml of MBS and then, the LT-activity in the supernatant liquid in the cultured solution was measured. As a result, fraction No. 13 was found to have the maximum LT-activity. Accordingly, the sedimentation coefficient of the mRNA corresponding to LT was confirmed to be 12.6S to 14.6S on the basis of the calibration curve formed by the use the sedimentation coefficient standard markers (5S, 18S, 28S).

The purified mRNA as obtained in this example was used in the following experiment.

EXAMPLE 3

(1) Synthesis of cDNA

Using 5 μg of the pure mRNA, the reverse transcriptase system [$^{32}$P] (by New England Nuclear Co.) was partly modified to obtain cDNA. More precisely, a system containing 20 μl of reverse transcriptase reaction buffer, 10 μl of deoxynucleoside triphosphate mixture, 20 units of ribonuclease/A inhibitor, 10 μg of oligo(dT)$_{12-18}$' primer, 5 μl of 600 mM-β-mercaptoethanol, [α-$^{32}$P]dCTP (relative activity: 800 Ci/mmol (100 μCi)), 5 μg of mRNA and 50 units of avian myeloblastosis virus-derived reverse transcriptase was reacted in a volume of 100 μl, at 42° C. for 1 hour, and then, the whole was cooled with ice to terminate the reaction. After centrifugation, the hybrid of mRNA and cDNA were heat-treated in a boiling water bath for 3 minutes for separation, then rapidly cooled in an ice bath for 5 minutes.

The denatured protein was subjected to centrifugation (12000×g, 2 minutes) to form pellets, which were again cooled with ice. To 99 μl of the reaction solution were added, after the termination of the reaction, 16.2 μl of germ-free distilled water, 46.8 μl of DNA polymerase I reaction buffer, 10.4 μl of deoxynucleoside triphosphate mixture, [α-$^{32}$P]dCTP (800 Ci/mmol (100 μCi)) and 15.6 μl of *E. coli*-derived DNA polymerase I (8000 units/ml), while being cooled with ice, to make the total volume of the resulting mixture 198 μl. This was well stirred and centrifuged and then reacted for 20 hours at 15° C. After the reaction, 39.4 μl of 0.2M-EDTA$_{2Na}$ was added to 197 μl of the reaction solution to terminate the reaction, and 1N-NaOH (49.25 μl) was added thereto for alkaline-heat treatment at 65° C. for 1 hour to decompose the mRNA, and after being cooled with ice and centrifuged, 1M of Tris-HCl buffer (49.25 μl, pH 8.0) and 1N-HCl (49.25 μl) were added thereto for neutralization.

This was extracted with ½ equivalent of water-saturated phenol and ½ equivalent of chloroform/isoamyl alcohol (50:1), and, after being centrifuged, the upper separated layer was taken out. One equivalent amount of 10 mM-Tris-HCl buffer (containing 100 mM-NaCl and 1 mM-EDTA$_{2Na}$ and having a pH of 8.0) was added to the lower layer for re-extraction, and the upper layer as separated was also taken out. The two upper layers thus taken out were combined and extracted with one equivalent amount of chloroform/isoamyl alcohol and centrifuged, and the lower layer (organic layer) as separated was removed. This extraction was repeated four times, and then, the resulting extract was further extracted with one equivalent amount of water-saturated ethylene three times and the organic layer was removed. Afterwards, the remaining extract was heat treated in a hot water-bath at 60° C. to remove the ethylene therefrom.

The resulting aqueous layer was concentrated with sec-butanol, and MgCl$_2$ having a final concentration of 0.01M and two equivalents of cold ethanol (−20° C.) were added thereto and kept at −80° C. for one night. The resulting mixture was subjected to centrifugation (12000×g) for 10 minutes, and the resulting precipitate was dried under reduced pressure and dissolved in 50 μl of germ-free distilled water. To the resulting solution were added 20 μl of reverse transcriptase reaction buffer, 5 μl of 600 mM-β-mercaptoethanol, 10 μl of deoxynucleoside triphosphate mixture and [α-$^{32}$P]dCTP (800 Ci/mmol (100 μCi)) and the mixture was well stirred, and after being centrifuged, 5 μl of the above-mentioned reverse transcriptase was added thereto and reacted for 1 hour at 42° C. The reaction was terminated under cooling with ice, to obtain the complete cDNA having a hair-pin loop structure.

To 99 μl of the above-mentioned reaction solution were added 92.1 μl of germ-free distilled water, 23.4 μl of the above-mentioned DNA polymerase I reaction buffer, 55 μl of S$_1$ nuclease reaction buffer and 5.5 μl of Aspergillus oryzae-derived S$_1$ nuclease (50 units/ml) and the mixture was reacted for 30 minutes at 37° C. to cleave the hair-pin loop structure of the cDNA to obtain a double-stranded cDNA. To this solution was added 46 μl of 0.1M-Tris-HCl buffer (containing 0.1H-EDTA$_{2Na}$ and having a pH of 7.5), and the resulting solution was fed into Sephacryl S-200 column (size: 1.0×25 cm) having a bed capacity of 20 ml and subjected to elution with 10 mM-Tris-HCl buffer (containing 0.1M-NaCl and 1 mM-EDTA$_{2Na}$ and having a pH of 7.5). The fractionation was carried out to obtain fractions each having a volume of 300 μl, and the fraction which dissolved out near the void volume was concentrated with sec-butanol, and it was subjected to ethanol-precipitation to recover cDNA.

(2) Preparation of Oligo(dC)tail-added cDNA

To the double-stranded cDNA obtained above was added 160 μl of a reaction buffer having the following composition, and the mixture was reacted for 5 minutes at 37° C., whereby the oligo(dC)tail was added to the double-stranded cDNA.

The reaction buffer is 0.2M-potassium cacodylate 25 mM-Tris-HCl buffer (pH 6.9) containing 2 mM of DTT, 5 mM of CoCl$_2$, 0.25 mg/ml of BSA, 5 μM of dCTP, $^3$H-labeled dCTP (25 Ci/mmole (15 μCi)) and 30 units of terminal deoxynucleotidyl transferase.

The reaction was terminated by cooling with ice, and one equivalent of water-saturated phenol/chloroform/isoamyl alcohol (50:50:1) was added to the reaction solution for extraction. The resulting extract was again extracted with chloroform/isoamyl alcohol (50:1), and 40 μg of *E. coli*-derived ribosome RNA and 1/50 equivalent of 5M-NaCl were added to the extract, and thereafter 2 equivalents of cold ethanol were added thereto and kept at −80° C. for one night. The oligo(dC)tail-added cDNA was recovered by centrifugation and dissolved in germ free distilled water to obtain a solution having a concentration of 0.5 ng/μl.

(3) Formation of Recombinant Plasmid 1.375 ng of the oligo(dC)tail-added cDNA and 10 ng of oligo-(dG)$_{10-20}$tail-added pBR322 DNA (made by Amersham) were incubated in 25 μl of annealing solution (10 mM-Tris-HCl buffer containing 100 mM of NaCl and 0.1 mM of EDTA$_{2Na}$ and having pH of 7.8), at 65° C. for 15 minutes, and then, the incubator was regulated at 45° C. and the whole was further incubated for 2 hours at 45° C. Afterwards, this was cooled with ice for annealing, to obtain a recombinant plasmid-containing solution.

(4) Selection of Transformant

The recombinant plasmid solution as obtained in the above was applied to E. coli HB101 strain for transformation. More precisely, E. coli HB101 strain was incubated in 10 ml of L-broth containing 0.1% of glucose at 37° C. until the absorbance of the cultured medium (650 nm) reached 0.05, and 5 ml of the cultured solution was added to 500 ml of 0.1%-glucose-containing L-broth and further incubated until the absorbance (650 nm) reached 0.3. After cooling with ice for 30 minutes, this was centrifuged at 4° C. for 5 minutes at 3000 rpm (with RPR 9-2 Rotor by Hitachi Co.) to collect the grown bacteria. The bacteria were dispersed in 250 ml of a cold 50 mM-CaCl$_2$ and cooled for 15 minutes with ice. This was subjected to centrifugation by the use of RPR 9-2 Rotor (4° C., 5 minutes, 2500 rpm), and the collected bacteria were dispersed in 25 ml of 50 mM-CaCl$_2$ containing 20% glycerol, and the resulting dispersion was divided into vials each having a content of 1 ml and freeze-dried with a dry-ice powder and then preserved at −80° C. The preserved bacteria dispersion was thawed while being cooled with ice, and 0.3 ml of the thus thawed bacteria dispersion was blended with 0.15 ml of the above-mentioned recombinant plasmid solution and 0.15 ml of 20 mM-CaCl$_2$/60 mM-MnCl$_2$/20 mM-RbCl solution and kept still at 0° C. for 20 minutes and then at room temperature for 10 minutes. Afterwards, 2.4 ml of 0.1%-glucose-containing L-broth which had previously been warmed at 37° C. was added thereto and blended, and the whole was incubated for 1 hour at 37° C. while being shaken. A part of the thus incubated solution was taken out, and this was spread over L-broth/agar plate containing 15 µg/ml of tetracycline in addition to the above-components and incubated thereon at 37° C. for about 12 hours, and tetracycline-resistant bacteria were selected to form a cDNA library.

(5) Hybridization Test

In order to screen the transformant having the plasmid containing the LT-encoding cDNA, the above-mentioned cDNA library was subjected to a colony-hybridization test using $^{32}$P-labeled synthetic cDNA-probes. For the formation of the synthetic cDNA probes, 18 bases (404th to 421st base) (5'-GTCTACTCCCAGGTGGTC-3') and the complementary base sequence (5'-CACATGGAAGGGGTACTG-3') corresponding to 18 bases (500th to 517th base) in the LT-gene reported by Gray, et al. (Nature, 312, 721 (1984)) were chemically synthesized, and 16.6 pmol thereof was reacted with 5 units of T4 phage-infected E. coli-derived poly-nucleotide-kinase and [γ-$^{32}$P]ATP (5 µCi/pmole (20 µCi)) in 50 mM-Tris-HCl buffer (containing 10 mM of MgCl$_2$, 5 mM of DTT, 0.1 mM of spermidine and 0.1 mM of EDTA$_{2Na}$ and having pH of 7.6), at 37° C. for 30 minutes.

The reaction was terminated by adding EDTA solution to the reaction solution and cooling the same with ice at 0° C. These two kinds of $^{32}$P-labeled cDNA probes were used in the hybridization test, and the transformants having a recombinant plasmid capable of being hybridized with both of the two probes under weak conditions were selected. Thus, 6 colonies were selected out from about 10,000 colonies.

Next, the recombinant plasmid was separated out from the thus selected 6 strains, and this was cleaved with restriction enzyme HindIII, subjected to agarose gel electrophoresis, transferred to nitrocellulose filter and then again hybridized with the $^{32}$P-labeled synthetic cDNA probes under a severe condition. As a result, one clone was selected out.

Next, the thus selected strain was subjected to a hybridization-translation test, in accordance with the method described in Maniatis T, et al., Molecular Cloning, 329 (1980) (Cold Spring Harbor Laboratory). The plasmid DNA was extracted out from the transformant strain and, after being heated and denatured, it was fixed on a nitrocellulose filter, and the LT mRNA-containing mRNA fraction obtained in the previous Example 2-(4) was added thereto and reacted for 3 hours at 50° C. for hybridization. The bonded mRNA was recovered by elution, and then, it was injected into oocytes in the same manner as the previous Example 2-(3), and then, the recovered mRNA was checked as to whether or not it was LT-mRNA.

As a result, 10 U/ml of LT was detected in the case of the pLT13, whereas no LT-activity was detected in the control case of pBR322.

This cDNA was cleaved with restriction enzyme HindIII, and the size thereof was measured by agarose gel electrophoresis, and as a result, it was confirmed to contain a cDNA part of about 1.35 Kbp.

The transformant containing this cDNA (Strain Number: LT 13, Cloned DNA Number: pLT 13) was treated for the isolation of the cloned DNA, and the base sequence thereof was determined by the method mentioned below.

EXAMPLE 4

Determination of Nucleotide Sequence of Cloned DNA (1) Formation of Restriction Endonuclease Cleavage Map The strain (LT 13) obtained in the previous Example 3-(5) was incubated in L-broth containing 0.1% glucose and 15 µg/ml tetracycline to obtain bacteria. Plasmid DNA was recovered from the bacteria, and the restriction endonuclease cleavage map thereof was obtained with restriction enzymes EcoRI, SmaI, BamHI, PstI, SalI and HindIII which can be introduced into M13mp 8, 9 to be mentioned in the following item. (See FIG. 1.)

(2) Determination of Nucleotide Sequence of Cloned DNA

For the determination of the nucleotide sequence of cloned DNA, the cDNA fragment was sub-cloned with M13mp 8 or mp 9 in accordance with the method of Messing et al. (Gene, 19, 269 (1982)) and then processed in accordance with the method of Sanger et al., the dideoxy chain termination method (Proc. Natl. Acad. Sci. USA, 74, 5463 (1977); J. Mol. Biol., 162, 729 (1982)) for annealing of primer, synthesis of complementary chain with Klenow fragment of DNA polymerase I (as labeled with α-$^{32}$P-labeled dCTP (800 Ci/mmol (20 µCi)), gel electrophoresis and auto-radiography.

Figure 2:
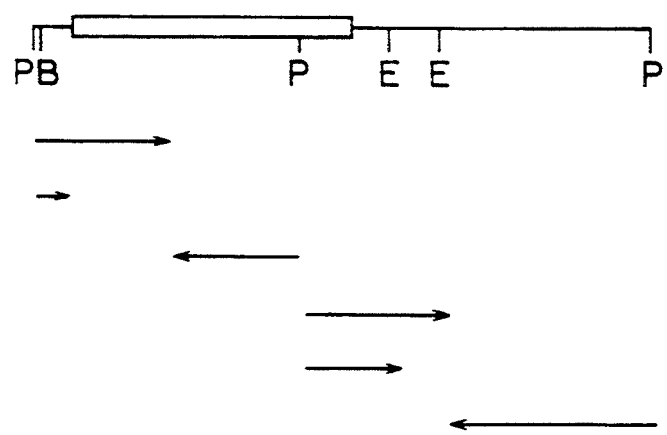

FIG. 2 shows the restriction enzyme-cleaved sites as used for the determination of the nucleotide sequence, the direction for the determination of the nucleotide sequence and the range thereof being designated by arrows therein. The part designated by the rectangle therein shows the part encoding the translation range of LT.

The nucleotide sequence is as shown in the previous Table 1. There are 16 G-linkage tail in the upstream of the first C and 18 C-linkage tail in the downstream of the 1310th T, and these are homopolymers synthesized when added to the vector. The 63 to 677th bases form a nucleotide sequence which is assumed to encode the necessary polypeptide for constituting the LT-precursor.

Among these bases, those from the 165th base are considered to encode LT, and the nucleotide sequence is different from that of LT as reported by Gray P. W. et al. (Nature, 312, 721 (1984)) in that the 26th amino acid is Asn(AAC) in the former while the amino acid is Thr(ACC) in the latter. The present sequence has the terminal codon (TAG) following the C-terminal amino acid (leucine). In addition, the present sequence is further different from Gray et al's sequence in parts other than the peptide-encoding part, in that the 1st to 4th bases are CGGG in place of GGTC, that the 862th to 865th bases are ACAC in place of CACA and that the 1306th to 1310th bases are CCCCT in place of TGAAA.

EXAMPLE 5

(1) Cleavage of cDNA Fragment of pLT 13 With Restriction Enzymes

Based upon the structure of the complete cDNA, the restriction enzymes PvuII (190th base) and EcoRI (838th base) were used. pLT13 was cleaved with the said restriction enzymes in a conventional manner and subjected to 1.5% agarose gel electrophoresis, whereby a cDNA fragment of about 650 bp was then extracted out from the agarose gel. This cDNA fragment was subjected to water-saturated phenol-extraction and chloroform/isoamyl alcohol-extraction, followed by ethanol-precipitation, to recover the cDNA fragment. This cDNA fragment lacks 28 bases at its N-terminal end as compared with the from C which N-terminal of LT, and therefore, this fragment contains up to 164 bases downstream of the stop codon.

(2) Cleavage of Polylinker Site of Phenotypic Expressing Vector pKK223-3 (Obtained From Pharmarcia Co.) With Restriction Enzymes:

The polylinker site of pKK223-3 (4585 bp) was initially completely cleaved with EcoRI and then partially cleaved with BamHI. The DNA fragment of the pKK223-3 which was completely cleaved with BamHI was isolated by 1.5% agarose gel electrophoresis, and the remaining parts were subjected to agarose gel extraction, phenol extraction, chloroform/isoamyl alcohol extraction and ethanol precipitation in this order. Thus the plasmid, partially cleaved with BamHI, and the vector, which was not cleaved with BamHI, were recovered. Next, these plasmids were completely cleaved with SmaI, to obtain the cleaved EcoRI-BamHI site and EcoRI-SmaI site.

(3) Ligation of Portable Translation Initiating Site (PTIS: Top Chain (EcoRI) : Bottom Chain (BamHI), by Pharmarcia Co.) and EcoRI-BamHI Site Cleaved pKK223-3

The EcoRI-BamHI site-cleaved vector of pKK223-3, as obtained in (2) above, and PTIS (in which the top chain and the bottom chain had previously been heated at 65° C. for 5 minutes in 0.01M-Tris-HCl buffer, containing 0.1M NaCl and 0.1 mM EDTA$_{2Na}$ and having pH 7.8, transferred to a water bath at 37° C. for 1 hour, followed by incubation at room temperature for 20 minutes for annealing and then successively preserved at −20° C.) were reacted for one night at 14° C. in 50 mM-Tris-HCl buffer (containing 10 mM MgCl$_2$, 10 mM dithiothreitol and 1 mM ATP, pH 7.6) with T4 phage-infected E. coli-derived DNA ligase, in order to re-form a vector having a circular structure. This re-formed plasmid was introduced into E. coli strain JM 105 in a conventional manner for transformation, and the resulting transformant strains were spread over ampicillin-containing LB-agar medium. The bacteria containing the thus re-formed plasmid were then selected as ampicillin-resistant bacteria, and the plasmid was then obtained in a conventional manner. This plasmid was called PP-3.

(4) Cleavage of PP-3 With Restriction Enzymes and Blunt End Ligation Thereof With cDNA Fragment Initially, PP-3, as obtained in (3) above, was partially cleaved with BamHI and then reacted with bovine intestine mucosa-derived alkaline phosphatase (obtained from Pharmacia Co.) in 50 mM Tris-HCl buffer (containing 1 mM MgCl$_2$, 0.1 mM ZnCl$_2$ and 1 mM spermidine, pH 9.0), at 37° C. for 30 minutes for 5'-terminal dephosphorylation. Extractions followed with water saturated phenol, and with CIA (chloroform-/isoamyl alcohol). Precipitation with ethanol was then carried out to recover the open circular plasmid, and the cohesive end thereof was then converted to a blunt end by the use of DNA polymerase I (Klenow fragment). This plasmid having a blunt end was then recovered by extraction with water-saturated phenol, extraction with CIA and precipitation with ethanol.

The EcoRI-PvuII-fragment of pLT13, as obtained in (1) above, was treated with DNA polymerase I (Klenow fragment), which produced a blunt end, and the fragment was then recovered by extraction with phenol, extraction with CIA and precipitation with ethanol in this order. The recovered fragment was then ligated with the blunt end-containing open circular PP-3 plasmid in the presence of DNA ligase at 16° C. for 20 hours. After the reaction, the closed circular plasmid was recovered by extraction with water-saturated phenol, extraction with CIA and precipitation with ethanol in this order, and the plasmid was introduced into E. coli strain JM 105 in a conventional manner for transformation. By the use of an ampicillin-containing LB medium, 5300 transformants were selected.

(5) Screening With Synthetic cDNA Probe

The transformants as obtained in the (4) above, were screened by a colony-hybridization test using a $^{32}$P-labeled synthetic cDNA probe, in the same manner as in Example 3-(5), in which 100 colonies were selected. A plasmid was prepared from 20 colonies in a conventional manner, and this plasmid was cleaved with restriction enzymes (BamHI and HindIII) and then subjected to agarose gel electrophoresis. The desired plasmid containing DNA fragments of about 650 bp and about 250 bp was located. As a result, the desired three colonies were selected.

(6) Expression of LT in E. coli

Figure 3:
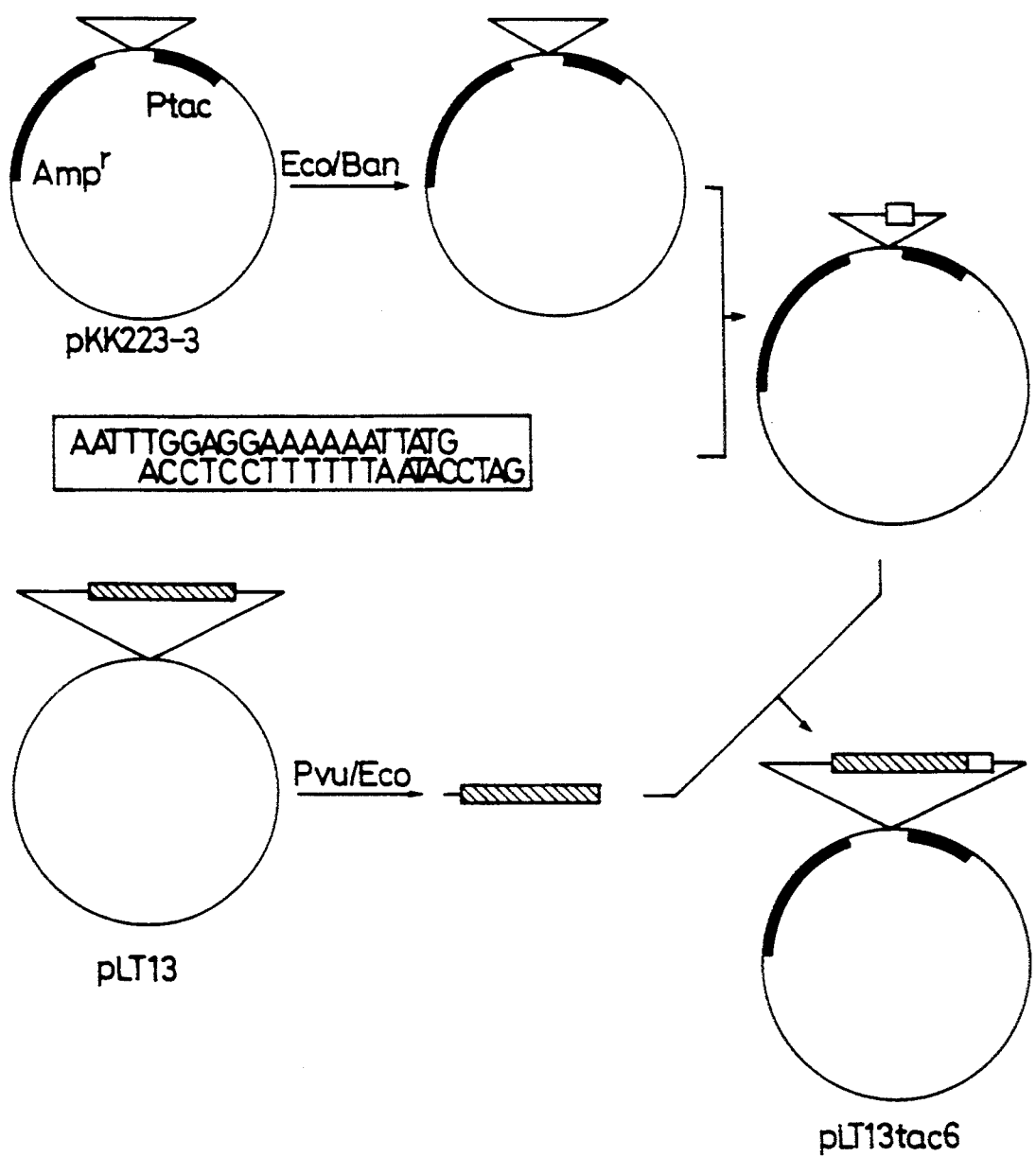

One of the three transformants as obtained in (5) above, was used for the LT-expression. The tac promoter of the plasmid as inserted into the host bacteria of E. coli strain JM 105 was suppressed in the said host bacteria, but the suppression can be eliminated by the addition of IPTG. The transformants were incubated in LB-medium (composition: 10 g bacto-tryptone, 5 g bacto-yeast extract and 10 g NaCl in one liter, pH 7 to 7.5, containing 25 mg of ampicillin) which contained 0 to 1 mM of IPTG, until an O.D. (550 nm) of 1.1 to 1.2 was reached. The bacteria thus incubated were collected by centrifugation and washed with a physiological salt solution, buffered with a phosphate buffer (hereinafter referred to as PBS). The bacteria were again collected by centrifugation and then suspended in PBS such that O.D. (550 nm) was 1.0. The resulting suspension was treated with ultrasonic waves to disintegrate the bacteria therein. The suspension was filtered under germ-free conditions, and the LT-activity was measured. In the case of no addition of IPTG, the LT-activity was $0.26 \times 10^4$ U/ml; upon the addition of IPTG at concentrations of 0.01 mM, 0.1 mM and 1 mM, the LT-activity was $11 \times 10^4$, $10 \times 10^4$ and $15 \times 10^4$ U/ml, respectively. However, when the same test was carried out using pKK223-3-inserted bacteria as a control, no LT-activity was detected. Thus, the expression of the LT-activity was demonstrated to result from the the insertion of the recombinant plasmid into the host bacteria. The strain number of the transformant as used herein was called LT13tac6, and the plasmid as inserted thereinto was called pLT13tac6. FIG. 3 shows the process for the formation of pLT13tac6.

EXAMPLE 6

The transformant LT13tac6-strain was incubated in M9-minimal medium containing 19 essential amino acids (except proline) overnight, and the cultured solution was inoculated into 10 times the amount of LB-medium. After 2.5 hours, IPTG was added to a final concentration of 0.1 mM, and the incubation was continued for an additional 3 hours. The bacteria were then collected by ultra-filtration and centrifugation. 90 g (wet weight) of the bacteria were suspended in 300 ml of 50 mM-Tris-HCl (pH 8.0) containing 30 mM NaCl and 0.01 mM p-APMSF (p-aminophenylmethane sulfonyl fluoride hydrochloride, made by Wake Junyaku KK) and were disintegrated by ultrasonic treatment. The resulting suspension was subjected to centrifugation to remove residual bacteria, and the supernatant liquid was a crude extract. The total LT-activity of 347.5 ml of the crude extract was $12.2 \times 10^8$ U, and the relative activity thereof was $9 \times 10^4$ U/mg protein.

EXAMPLE 7

Purification of LT-Polypeptide (1) Ammonium Sulfate Salting-Out

Ammonium sulfate was added to 347 ml of the crude extract to produce a 40%-saturated solution at 5° C. After incubation at 5° C. for 30 minutes, the solution was subjected to centrifugation. The precipitate formed was dissolved in 100 ml of 5 mM-phosphate buffer (pH 7.4) (hereinafter referred to as PB), and the resulting solution was subjected to dialysis against 4 liter volumes of 5 mM-PB with four changes. After dialysis, the solution was used as the ammonium sulfate salted-out sample. The total LT-activity of 117 ml of the sample was $11.7 \times 10^8$U, and the relative activity thereof was $4.6 \times 10^5$ U/mg (protein).

(2) Anionic Exchange Chromatography 116 ml of the ammonium sulfate salted-out sample was loaded onto a column (2.6×34 cm) of DEAE-Sepharose CL-6B (made by Pharmacia Co.) which had previously been equilibrated with 5 mM of PB (pH 7.4). The column was then washed with 400 ml of 5 mM-PB (pH 7.4) and the sample in the column was eluted with an increasing salt gradient, the concentration of which increased from 0 to 0.3M. The resulting eluent was collected in of 25 ml aliquots, and the LT-activity of each fraction was measured. By this means, the fractions having the LT-activity were recovered. About 1000 ml of the recovered solution was concentrated on an ultrafiltration membrane (fractionating molecular weight: 10,000, made by Millipore Co.) to 88 ml. The concentrated solution was labelled as the DEAE fraction solution. The total LT-activity of the DEAE fraction solution was $4.4 \times 10^8$U, and the relative activity thereof was $8.27 \times 10^6$ U/mg protein.

(3) Hydrophobic Chromatography 85 ml of the DEAE fraction solution was adsorbed to a column (2.6×14 cm) of phenyl-Sepharose CL-6B (made by Pharmarcia Co.) which had previously been equilibrated with PBS and then washed with 150 ml of 10 mM-PB (pH 7.4) containing 30% of ethylene glycol. The column was then eluted with ethylene glycol, the concentration of the ethylene glycol eluate being continuously elevated from 30% to 70%. The resulting eluent was fractionated into 15 ml aliquots, the functions were then dialyzed against PBS, and the LT-activity of each fraction, was measured. The fractions having the LT-activity were thus recovered. 308 ml of the recovered solution was concentrated by the above-mentioned ultrafiltration to 9.4 ml, and the thus concentrated solution was named as the phenyl fractionated solution. The total LT-activity of the phenyl-fractionated solution was $3.94 \times 10^8$U, and the relative activity thereof was $5.63 \times 10^7$ U/mg protein.

The resulting fraction was treated with Britton-Robinson buffer of a broad concentration range (Britton and Robinson; J. Chem. Soc., 1931, 458, 1456) to regulate the pH value to a determined value and then incubated for 24 hours at 4° C. The thus incubated solution was subjected to dialysis against PBS for 24 hours, and the LT-activity thereof was measured, whereupon the LT-concentration in each buffer was 4.6 μg/ml. As a result, 98% or more of the LT-activity was lost at pH 2, while no deterioration of the LT-activity occurred in pH range 4 to 10. The phenyl-fractionated solution was analyzed by 0.1% SDS polyacrylamide-gel electrophoresis (SDS-PAGE). (Refer to Laemmli, U. K. Nature, 227, 680 (1970).) The LT-activity appeared in a protein peak corresponding to a molecular weight of about 17,500; as determined by silver-staining. The molecular weight markers used on the SDS-PAGE were:

Phosphorylase B; MW 94,000, BSA: MW 67,000, Ovalbumin: MW 43,000, Carbonic anhydrase: MW 30,000, Soybean trypsin inhibitor: MW 20,000, α-lactalbumin: MW 14,400.

EXAMPLE 8

The phenyl-fractionated solution was further concentrated to ¼ the original volume by ultrafiltration, and 0.5 ml of the concentrated solution was fractionated on SDS-PAGE (gel plate: 1.5 mm×16 cm×14 cm). The gel fraction corresponding to a molecular weight of 17,500 was cut out and extracted with tris-acetate buffer (pH 8.6). This operation was repeated, and the resulting extracts were combined and concentrated by ultrafiltration on a membrane having a fractionating molecular weight of 5,000 (made by Amicon Co.) and then subjected to dialysis. This was a purified LT-polypeptide LT(I). The amino acid composition, the N-terminal amino acid sequence and the isoelectric point of the purified LT-polypeptide LT(I) were measured, as follows:

(1) Amino Acid Composition

LT(I) was dried to a solid under reduced pressure. 6N-HCl was added to this solid and the mixture was hydrolyzed at 110° C. for 6 hours. Next, this was reacted with phenyl-isothiocyanate to obtain PTC-amino acid, and then, the composition thereof was analyzed by the use of an amino acid analyzer (reverse phase partition method, by Waters Co.). The tryptophan and cysteine were quantitatively determined by the method of Inglis (Methods in Enzymology, Vol. 91, p. 26, edited by Hirs, C. H. W. et al, Academic Press, 1983). The result is given in Table 4.

The analyzed data corresponds well with the amino acid composition as obtained from the nucleotide sequence of DNA encoding LT-polypeptide.

TABLE 4

| Amino acid composition of LT(I) | | |
|---|---|---|
| Amino acid | Analyzed data (mol) | Amino acid composition obtained from nucleotide sequence (mol) |
| ILE | 2.8 | 3 |
| VAL | 9.1 | 9 |
| LEU | 21.5 | 21 |
| PHE | 9.9 | 10 |
| CYS | <0.1 | 0 |
| MET | 3.9 | 4 |
| ALA | 15.0 | 15 |
| GLY | 8.6 | 9 |
| THR | 7.7 | 8 |
| TRP | 1.6 | 2 |
| SER | 20.5 | 20 |
| TYR | 6.8 | 27 |
| PRO | 12.4 | 13 |
| HIS | 10.3 | 10 |
| GLU } GLN | 14.4 | 2 / 12 |
| ASP } ASN | 10.1 | 5 / 5 |
| LYS | 6.1 | 6 |
| ARG | 2.7 | 3 |

(2) N-terminal Amino Acid Sequence

The N-terminal amino acid sequence was determined by Edman's method (Edman, P.; Arch. Biochem. Biophys., 22, 475 ( 1949 ) ).

LT(I) (about 100 µg) was reacted with phenyl-isothiocyanate by a coupling reaction, and then, the N-terminal amino acid was cleaved in the form of a 2-anilino-5-thiazolinone derivative, which was further converted into a phenylthiohydantoin-amino acid. This was identified by the use of HPLC (made by Waters Co.) using a C18-reversed phase column to determine the N-terminal amino acid. This operation was repeated in order that the amino acid sequence of the N-terminal part was determined. The resulting amino acid sequence of the N-terminal part of LT(I) was as follows:

MET—ASP—PRO—ALA—GLN—THR—ALA—ARG—GLN—HIS—PRO—LYS—MET—HIS—LEU—
ALA—HIS—SER—ASN—LEU—LYS—

(3) Measurement of Isoelectric Point

The isoelectric point of LT(I) was measured by means of isoelectrophoresis using a flat gel containing Pharmalite (by Pharmacia Co.) and 5%-polyacrylamide and having a pH range of 5.0 to 8.0. The resulting isoelectric point of LT(I) was 7.6±0.3.

The electrophoresis was carried out at 2000V, for 4.5 hours. The gel was cut into 3 mm pieces and extracted with PBS (pH 7.4), and the LT-activity was measured. LT-activity occurred in the pH range of 7.6±0.3. The calibration curve was formed by using β-lactoglobulin-A (pI 5.20), bovine carbonic anhydrase-B (pI 5.85), human carbonic anhydrase-B (pI 6.55), horse myoglobin-acid side band (pI 6.85) and horse myoglobin-base side band (pI 7.35) as pH markers.

EXAMPLE 8'

Balb/c mice (8 weeks old females; purchased from Nippon Charles River) were inoculated, by subcutaneous injection into the right inguinal region, with Meth A mouse tumor cells at an inoculum size of $1 \times 10^5$ cells per animal (day 0). On day 7, the tumor size was 40 to 60 mm$^2$. An LT preparation prepared by diluting the phenyl fractionated fraction obtained in Example 7 with PBS containing 100 µg/ml of gelatin was administered to the mice either intraveneously (i.v.) or intratumorally (i.t.) for consecutive 5 days beginning with day 7. Complete tumor disappearance was attained on day 25 in the i.v. group and on day 20 in the i.t. group at an LT dose of $1 \times 10^4$ units/mouse/day and of $5 \times 10^2$ units/mouse/day, respectively.

EXAMPLE 9

(1) Cleavage of cDNA Fragment of pLT13 With Restriction Enzymes

From among the restriction enzymes which are considered usable for the cleavage of the cDNA fragment of pLT13 in view of the structure of the complete cDNA thereof, NsiI (222nd base) and EcoRI (838th base) were selected, and the pLT13 was cleaved with the thus selected restriction enzymes in a conventional manner and subjected to 1.5% Agarose gel electrophoresis and a cDNA fragment of 616 bp was extracted from the Agarose gel. The cDNA fragment was purified in a conventional manner. This cDNA fragment is lacking 60 bases corresponding to 20 amino acid residues in the N-terminal side of LT.

(2) Ligation of Synthetic Oligonucleotide and LT-cDNA:

A synthetic oligonucleotide having the following structure (made by Applied Biosystem Co., as synthesized by the use of 381A-DNA Synthesizer) and the LT-cDNA fragment as obtained in the above step (1) were reacted by the use of T4-DNA ligase, in 66 mM Tris-HCl buffer (pH 7.6), 6.6 mM MgCl$_2$, 10 mM DDT and 1 mM ATP, at 16° C. for one night, whereby the synthetic oligonucleotide was linked with the LT-cDNA fragment.

Structure of Synthetic Oligonucleotide

AATTCTATGCA
GAT

The reaction product was purified in a conventional manner and then digested with EcoRI to recover the EcoRI fragment of 623 bp.

(3) Introduction of LT-cDNA Fragment into Expressing Vector

An expressing vector pKK223-3 (made by Pharmacia Co.) was digested with EcoRI and then reacted with a bovine intestine mucosa-derived alkaline phosphatase (made by Pharmacia Co.) in 50 mM Tris-HCl buffer (pH 9.0), 1 mM MgCl$_2$, 0.1 mM ZnCl$_2$ and 1 mM spermidine, at 37° C. for 30 minutes for 5'-terminal dephosphorylation and thereafter purified in a conventional manner. The vector thus treated was linked with the EcoRI fragment of 623 bp, as obtained in (2) above, and then, the resulting product was introduced into E. coli strain JM 105 in a conventional manner for transformation. By use of an ampicillin-containing LB medium, 8700 transformants were obtained.

(4) Screening With Synthetic cDNA Probe

Figure 4:
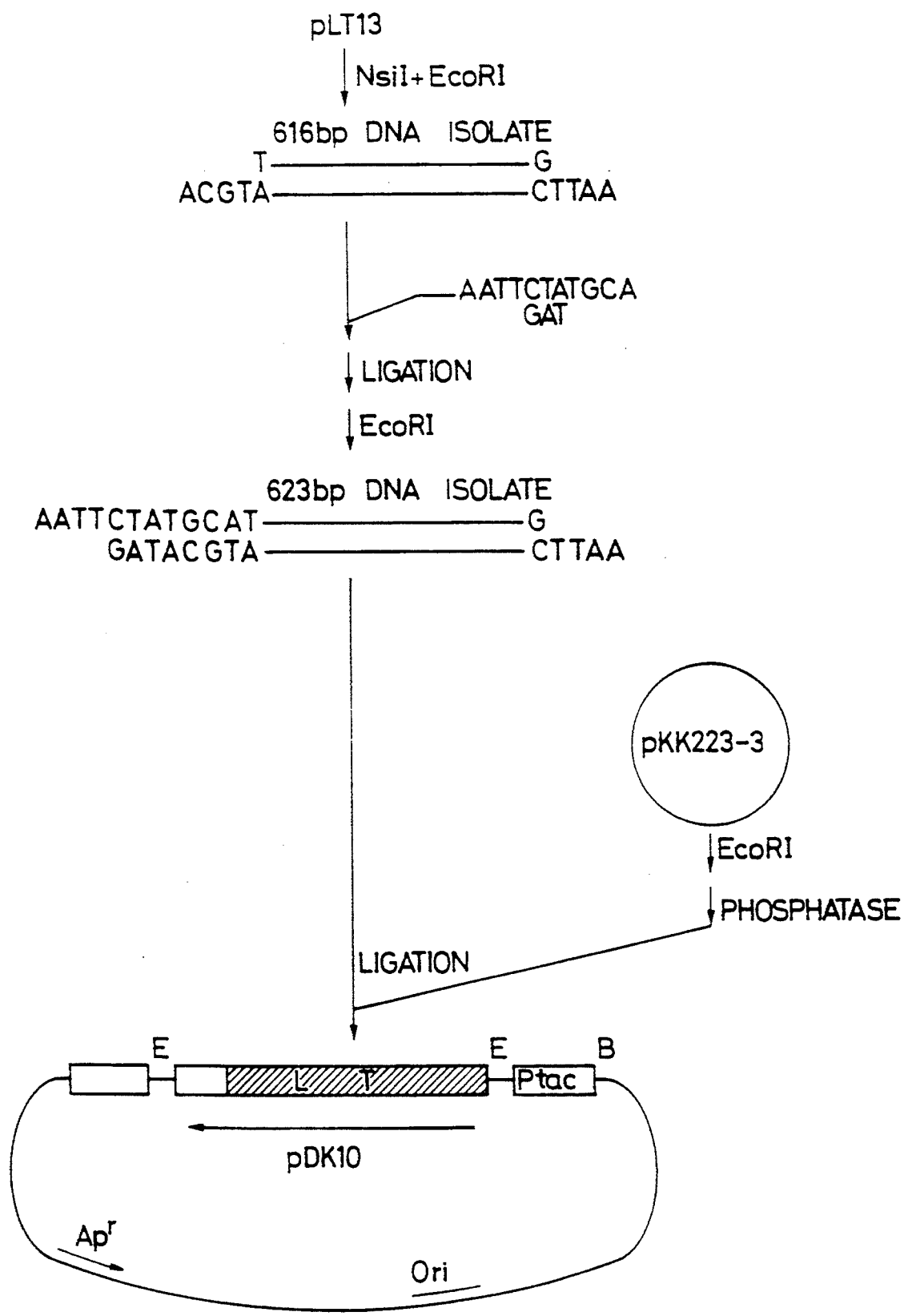

The transformants as obtained in (3) above, were screened by a colony-hybridization test using $^{32}$P-labeled synthetic cDNA-probe, in the same manner as the previous Example 3-(5), whereby 150 colonies were selected. 24 colonies were sampled at random from among these colonies, and a plasmid was prepared therefrom in a conventional manner. The plasmid was cleaved with the pertinent restriction enzymes and was then subjected to agarose gel electrophoresis, whereby the desired fragment and the direction thereof were detected. As a result, seven desired colonies were selected and the plasmid was called pDK10. The step for the formation of the pDK10 is shown in FIG. 4.

(5) Removal of 3'-Terminal Non-Coding Region of LT-cDNA

The plasmid pDK10 as obtained in (4) above, was digested with HindIII and then reacted with BAL31-nuclease (made by Takara Shuzo Co.) in 20 mM Tris-HCl buffer (pH 8.0), 12 mM CaCl$_2$, 12 mM MgCl$_2$, 1 mM EDTA and 600 mM NaCl, for 10 to 60 minutes at 30° C., in order to remove the DNA-terminal. Next, this plasmid was treated with DNA polymerase (Klenow fragment) to make the terminal smooth and then digested with EcoRI and fractionated by 5%-polyacrylamide gel electrophoresis to recover the fragment of about 480 bp or so (preferably 460 bp).

(6) Ligation of LT-cDNA and Linker

The DNA fragment as obtained in (5) above and HindIII-linker (made by Takara Shuzo Co.) were linked and then digested with HindIII and purified in a conventional manner.

(7) Ligation of LT-cDNA and Expressing Vector pKK223-3 was digested with EcoRI and HindIII, and then, the fragment of 4555 bp was isolated by 0.7% Agarose gel electrophoresis and purified in a conventional manner. This was linked with the EcoRI-HindIII-DNA fragment as obtained in (6) above, to form a vector containing LT-cDNA fragment. (This plasmid was called pDK11.) The step for the formation of the pDK11 is shown in FIG. 5.

(8) Introduction of LT-cDNA into Multi-Copy Vector

Figure 6:
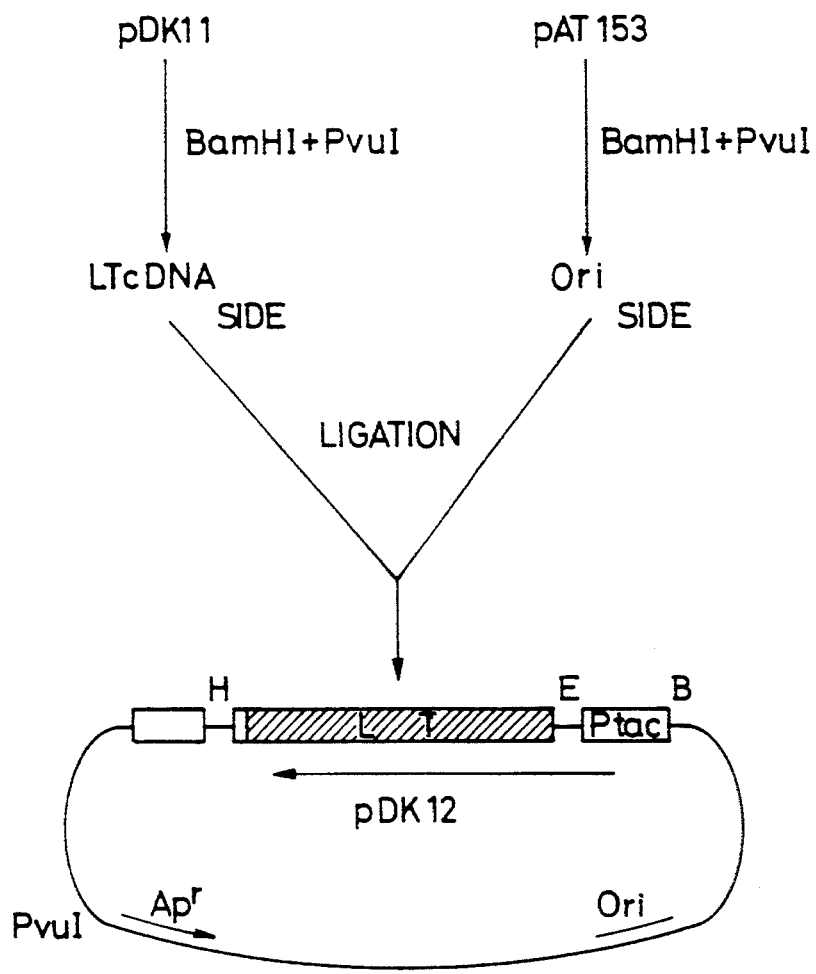

The plasmid as obtained in (7) above, was digested with BamHI and PvuI, and then, a fragment containing LT-cDNA was isolated and purified by Agarose gel electrophoresis. A plasmid pAT153 (commercial product by Amersham Co.) was also digested with BamHI and PvuI in the same manner and then, a fragment containing a DNA-replication initiating point was frationated and purified. These two kinds of BamHI-PvuI fragments were ligated and then introduced into E. coli JM 105 in a conventional manner for transformation. By use of ampicillin-containing LB-medium, 4300 transformants were selected. 24 colonies were sampled at random from among them, and a plasmid DNA was purified in a conventional manner. The plasmid was cleaved with pertinent restriction enzymes, whereby the number of the desired LT-cDNA fragments and the direction thereof were detected. As a result, 24 desired colonies were selected. (The plasmid was called pDK12.) The step for the formation of the plasmid pDK12 is shown in FIG. 6.

EXAMPLE 10

E. coli JM 105 transformed with pDK12 were pre-incubated in M9-medium containing 50 μg/ml of ampicillin and 19 amino acids (except proline) overnight. The next day, the pre-incubated solution was inoculated in LB-medium (comprising 10 g bacto-tryptone, 5 g bacto-yeast extract and 10 g NaCl in one liter, pH 7 to 7.5) containing 25 μg/ml ampicillin, the medium being diluted to 1/10 concentration because of the addition of the pre-incubated solution. After OD$_{550\ nm}$ reached 0.3, IPTG was added thereto to a final concentration of 1 mM, and then, the bacteria were further incubated until OD$_{550\ nm}$ reached 1. The cultured material was disintegrated by ultrasonic treatment and the LT-activity of the cell extract was measured. As a result, the LT-activity was about $3.5 \times 10^5$ units per ml of the cultured material.

EXAMPLE 11

E. coli JM 105 as transformed with pDK12 were incubated in M9-medium containing 50 μg/ml ampicillin and 19 amino acids (except proline) for one night, and then the cultured solution was further incubated in 20 times the volume of a medium comprising the composition shown below.

| Components | g/lit. |
| --- | --- |
| Na$_2$HPO$_4$ | 7.0 |
| KH$_2$PO$_4$ | 3.0 |
| (NH$_4$)$_2$SO$_4$ | 5.0 |
| Sodium citrate | 1.0 |
| MgSO$_4$ | 0.1 |
| Glucose | 25.0 |
| Casamino acid | 4.0 |
| Yeast extract | 4.0 |
| Thiamine | 0.1 |
| Ampicillin | 0.2 pH 7.5 |

After OD$_{550\ nm}$ of the medium reached about 10, IPTG was added to the medium to a final concentration of 5 mM, and then, the bacteria were further incubated until OD$_{550\ nm}$ reached 30. The cultured solution was recovered by ultrafiltration and centrifugation, and thus, 750 g (wet weight) of bacteria were recovered. The bacteria were suspended in 2000 ml of a mixture comprising 50 mM Tris-HCl buffer (pH 8.0), 30 mM NaCl and 0.01 mM (p-amidinophenyl)methanesulfonyl fluoride hydrochloride (made by Wako Junyaku Co.) and disintegrated by the use of a Dinor-mill, and then, subjected to centrifugation to obtain a crude extract solution. The total LT-activity of the crude extract solution (3700 ml) was $6.0 \times 10^{12}$ units, and the relative activity thereof was $5 \times 10^5$ units/mg protein.

EXAMPLE 12

(1) Ammonium Sulfate Fractionation

Ammonium sulfate was added to 3700 ml of the crude extract solution as obtained in Example 11 to 40% saturation at 5° C. After 30 minutes of incubation at 5°, the solution was subjected to centrifugation. The precipitate formed was dissolved in 500 ml of 5 mM-phosphate buffer (pH 7.8) (which is hereinafter referred to as PB), and the resulting solution was repeatedly subjected to concentration followed by dilution for salt removal, to obtain an ammonium sulfate salted-out sample. The total LT activity of 185 ml of the sample was $5.2 \times 10^{12}$ units and the relative activity thereof was $3.7 \times 10^6$ units/mg protein.

(2) Anionic Exchange Chromatography 184 ml of the ammonium sulfate salted-out sample was loaded onto a column (4.5 cm × 50 cm) of DEAE-Sepharose CL-6B (made by Pharmarcia Co.) which had previously been equilibrated with 5 mM PB (pH 7.8). The column was washed with 3.0 ι of 5 mM PB and the sample was eluted with a salt gradient, the concentration of the eluate solution being continuously increased from 0 to 0.3M. The resulting eluent was fractionated into 100 ml aliquots, and the LT-activity of each fraction was measured. The resultant fractions having the LT-activity were recovered. About 3.0 ι of the recovered solution was concentrated on an ultrafiltration membrane (fractionating molecular weight: 10,000, made by Millipore Co.) to 170 ml. The concentrated solution was named as DEAE-fractionated solution. The total LT-activity of the DEAE-fractionated solution was $2.9 \times 10^{12}$ units, and the relative activity thereof was $2.4 \times 10^7$ units/mg protein.

(3) Hydrophobic Chromatography 169 ml of the DEAE-fractionated solution was adsorbed to the content of a column (5.0 cm × 15 cm) of phenyl-Sepharose CL-6B (made by Pharmarcia Co.) which had previously been equilibrated with a physiological salt solution as buffered with 10 mM PB and then washed with 600 ml of 10 mM PB (pH 7.8) containing 30% of ethylene glycol. The column was eluted with ethylene glycol, the concentration of the ethylene glycol eluate being continuously elevated up to 70%. The ethylene glycol was removed from the recovered solution by the above-mentioned ultrafiltration. The eluent solution was then concentrated to 63 ml, and the concentrated solution was named as phenyl fractionated solution. The total LT-activity of the phenyl-fractionated solution was $2.3 \times 10^{12}$ units, and the relative activity thereof was $7.3 \times 10^7$ units/mg protein. The phenyl-fractionated solution was analyzed by means of 0.1% SDS polyacrylamide gel electrophoresis (SDS-PAGE). (Refer to Laemmli, U. K. Nature, 227, 680 (1970).) As a result, one band in the position of a molecular weight of 17,000 was identified by silver-dyeing. The molecular weight markers of SDS-PAGE were as follows:

Phosphorylase B: MW 94,000, BSA: MW 67,000, Ovalbumin: MW 43,000, Carbonic anhydrase: MW 30,000, Soybean trypsin inhibitor: MW 20,000, α-lactalbumin: MW 14,400.

EXAMPLE 13

The phenyl-fractionated solution was further concentrated to ⅓ by ultrafiltration, and 0.5 ml of the concentrated solution was fractionated by the use of SDS-PAGE (gel plate: 1.5 mm × 16 cm × 14 cm), and then the gel fragment corresponding to a molecular weight of 17,000 was cut out and extracted with tris-acetate buffer (pH 8.6). This operation was repeated, and the resulting extracts were combined and concentrated by the use of an ultrafiltration membrane having a fractionating molecular weight of 5,000 (made by Amicon Co.) and then subjected to dialysis. This was a purified LT-polypeptide LT(II). The amino acid composition and the N-terminal amino acid sequence of the purified LT-polypeptide LT(II) were measured, as follows:

(1) Amino Acid Composition

The purified LT(II) was dried to a solid under reduced pressure. 6N-HCl was added thereto and the mixture was hydrolyzed at 110° C. for 6 hours. This mixture was then reacted with phenyl-isothiocyanate to obtain PTC-amino acid, and the composition thereof was analyzed by an amino acid-analyzer (reversed phase partition method, by Waters Co.). The tryptophan and cysteine were quantitatively determined in accordance with A. S. Inglis' method (Methods in Enzymology, Vol. 91, p. 26, edited by Hirs, C. H. W. et al, Academic Press, 1983). The result is given in Table 5.

The analyzed data corresponds well to the amino acid composition as determined from the nucleotide sequence of DNA encoding LT-polypeptide.

TABLE 5

| | Amino acid composition of LT(II) | |
|---|---|---|
| Amino acid | Analyzed data (mol) | Amino acid composition obtained from necleotide sequence (mol) |
| ILE | 2.8 | 3 |
| VAL | 8.9 | 9 |
| LEU | 22.0 | 21 |
| PHE | 10.1 | 10 |
| CYS | <0.1 | 0 |
| MET | 3.1 | 3 |
| ALA | 11.8 | 12 |
| GLY | 9.1 | 9 |
| THR | 7.3 | 7 |
| TRP | 1.7 | 2 |
| SER | 19.4 | 20 |
| TYR | 6.8 | 7 |
| PRO | 12.2 | 11 |
| HIS | 10.1 | 9 |
| GLU | 12.0 | 2 |
| GLN | | 10 |
| ASP | 9.9 | 5 |
| ASN | | 5 |
| LYS | 5.0 | 5 |
| ARG | 1.9 | 2 |

(2) N-terminal Amino Acid Sequence

The N-terminal amino acid sequence was determined by Edman's method (Edman, P.; Arch. Biochem. Biophys., 22, 475 (1949)).

LT(II) (about 100 μg) was reacted with phenyl-isothiocyanate by a coupling reaction, and then, the N-terminal amino acid was cleaved off in the form of a 2-anilino-5-thiazolinone derivative, and was further converted into a phenylthiohydantoin-amino acid. This was identified by the use of HPLC (made by Waters Co.) using a C18-reversed phase column to determine the N-terminal amino acid. This operation was repeated and the amino acid sequence of the N-terminal part was thus determined. The resulting amino acid sequence of the N-terminal part of LT(II) was as follows:

MET-HIS-LEU-ALA-HIS-SER-ASN-LEU-LYS-
PRO-ALA-ALA-HIS-LEU-ILE-GLY-ASP

EXAMPLE 13'

Antitumor activity of LT(II) was evaluated in the same manner as in Example 8' using the phenyl fractionated solution obtained in Example 13. As a result, tumor disappeared completely on day 25 in the i.v. group and on day 20 in the i.t. group at an LT dose of $1 \times 10^4$ units/mouse/day and of $5\times10^2$ units/mouse/day, respectively.

EXAMPLE 14

Expression of LT Gene in Animal Cells (1) Preparation of cDNA Fragment

The strain LT13 as obtained in the previous Example 3-(5) was incubated in an L-broth medium to obtain grown bacteria. Plasmid DNA (pLT13) was recovered from the bacteria and cleaved with restriction enzyme XhoII and subjected to 1.5%-Agarose gel electrophoresis to recover a DNA fragment of about 940 bp in the same manner as the previous Example 5-(1). This DNA fragment is one containing 24th to 969th bases of the cDNA as shown in Table 1.

The cohesive end of this DNA fragment was converted into a blunt end by the use of a DNA polymerase I (Klenow fragment) and the fragment was recovered by phenol-extraction and CIA-extraction followed by ethanol-precipitation. This DNA fragment was ligated with BamHI linker d(CGGATCCG) (made by Takara Shuzo Co.), and thus, the DNA was recovered by phenol/CIA-extraction, CIA-extraction followed by ethanol-precipitation. This DNA was cleaved with restriction enzyme BamHI and subjected to 0.8% Agarose gel electrophoresis to recover DNA fragments of about 940 bp in the same manner as in Example 5-(1). These are considered to comprise a DNA fragment having BamHI linker-derived BamHI-cleaved terminal and a DNA fragment not having the same.

(2) Preparation of Expressing Vector (pSV2-Ecogpt-MMTV-LTR)

The cloning of MMTV-LTR was carried out in accordance with J. E. Majors and H. E. Varmus' method (Science, 289, 253 (1981)) or N. Fesel's method (EMBO J, 1, 3 (1982)).

Initially, a gene containing Ecogpt in the λ-phage was cloned in the form of EcoRI fragment of about 9 kb, and then, the PstI fragment which was a fragment of about 1.3 kb in the PstI site of pBR322 was sub-cloned. After the sub-cloning, the pBR322-MMTVLTR was partially digested with PstI and subjected to Agarose gel electrophoresis to recover the linear plasmid of about 6 kb in a conventional manner. The thus recovered plasmid was subjected to $S_1$-nuclease digestion, and the cohesive end thereof was converted into a blunt end, and then this was again recovered by Agarose gel electrophoresis. Further, this was ligated with a BamHI linker and then completely digested with BamHI and PstI. Afterwards, fragments of about 1.3 kb were isolated and recovered by agarose gel electrophoresis. The thus isolated fraction is considered to contain two kinds of DNA having a cohesive end of PstI-BamHI.

The pSV2-Ecogpt was prepared in accordance with Mulligan, R. C. and Berg, P. (Science, 209, 1422 (1980); Proc. Natl. Acad. Sci. USA, 78, 2072 (1981)). This plasmid is one containing a fragment of 2.3 kb which contains pBR322-derived replication origin and $Amp^R$ gene and SV40-derived early region promoter polyadenylation side and small antigen intron and containing XGPRT gene of E. coli (Ecogpt). This pSV2-Ecogpt was partially digested with PstI and completely digested with BamHI and then subjected to agarose gel electrophoresis to recover a fragment of about 4.9 kb. This fragment and the above-mentioned MMTV-LTR-containing PstI-BamHI fragment were ligated in a conventional manner, and then, transfected into HB101. These were selected under $Amp^R$ condition to obtain a desired transformant. A plasmid was recovered from the transformant in a conventional manner and this was digested with HindIII and SstI, and the resulting fragments were analyzed by Agarose gel-electrophoresis to obtain the desired plasmid pSV2-Ecogpt-MMTV-LTR capable of forming fragments of about 4 kb and about 2.2 kb.

(3) Preparation of pSV2-MMTV-LTR with LT-cDNA Fragment

Figure 7:
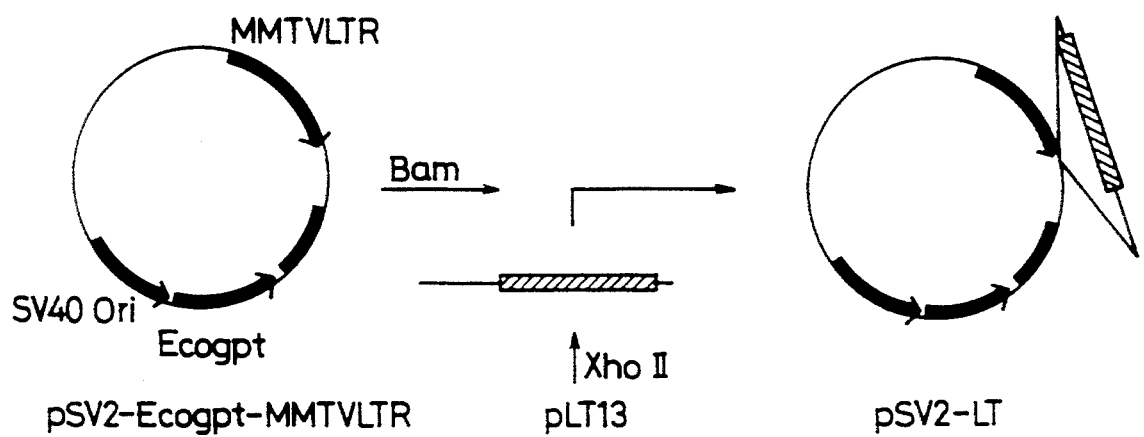
FIG. 7 shows steps for the formation of plasmid pSV2-LT/MMTV-LTR to be expressed in animal cells in Example 13, where the arrows designate the direction of the action of the promoter.

The cDNA fragment as obtained in step (3) and the pSV2-MMTV-LTR as obtained in step (2) were ligated by utilizing the blunt end of BamHI in the presence of T4 phage-infected E. coli-derived DNA ligase for transfection into E. coli HB101 strain. The bacteria were incubated in an ampicillin-containing L-broth agar-medium to obtain 300 transformant colonies. 20 colonies were picked up at random from among them, and these were pre-incubated in 1 ml of L-broth, and glycerin was added thereto and the thus incubated bacteria were preserved at $-20°$ C. Seven from among these 20 stock strains were inoculated in 10 ml of L-broth medium and incubated for one night at 37° C., and then the plasmids were recovered therefrom in a conventional manner. As a result of 0.8%-agarose gel electrophoresis, three clones were found to contain LT-cDNA fragment. These plasmids were further cleaved with a restriction enzyme EcoRI, and as a result, two clones containing LT-cDNA fragment as normally inserted into the lower flow of MMTV-LTR in the 5'- to 3'- direction and one clone containing the said fragment reversely inserted thereinto were obtained. The former plasmid was called pSV2-LT/MMTV-LTR. The step for the formation of the plasmid is shown in FIG. 7.

(4) Transfection of pSV2-LT/MMTV-LTR into Cos 1 Cells and LT-Expression

The transfection was carried out by utilizing a DNA calcium phosphate coprecipitation method, as follows:

24 hours prior to transfection, Cos 1 cells ($0.5\times10^6$ cells/5 ml(MEM-10%FCS medium)) were put in a disposable laboratory dish having a diameter of 6 cm and incubated at 37° C. under condition of 5% ($CO_2$)-95%(air) atmosphere. 4 hours prior to the transfection, the medium was exchanged and the cells were further incubated. Solution (A) (comprising 500 µl of $2\times$HBS (containing 10 g/l HEPES and 16 g/l NaCl pH 7.10) and 10 µl of $100\times PO_4$ (comprising an equivalent mixture solution of 70 mM $Na_2HPO_4$ and 70 mM $NaH_2PO_4$)) was prepared, and while air was being introduced thereinto, solution (B) (comprising 60 µl of 2M $CaCl_2$ and 440 µl of carrier DNA (salmon sperm-DNA)-containing plasmid aqueous solution having a final concentration of 20 µg/ml)) was dropwise added thereto and the mixture was kept at room temperature for 20 minutes for coprecipitation, 500 µl of the coprecipitated deposited was added to the above-mentioned Cos 1 cells-incubated solution and the cells were further incubated for 16 hours at 37° C. under the condition of 5%($CO_2$)-95%(air) atmosphere. The medium was exchanged, and dexamethasone was added thereto to final concentration of $1\times10^{-6}$M, and the incubation was further continued at 37° C. under the condition of 5%($CO_2$)-95%(air) for 24 and 48 hours. After the incubation, the supernatants were collected in each case. In the present test, the use of the plasmid DNA containing the LT-cDNA fragment in the normal direction in an amount of 2 µg, 1 µg and 200 ng for the transfection results in the yield of the LT-activity of 5.5, 2.3 and 1.9 U/ml, respectively.

On the other hand, the use of the other plasmid DNA containing the said fragment in the reverse direction results in no yield of the LT-activity. From these results, the expression of the LT-cDNA in animal cells was confirmed.

EXAMPLE 15

(1) Cleavage of LT cDNA With Restriction Enzymes

The cloned DNA (pLT13) obtained in Example 3 was introduced into *Escherichia coli* SK383 (a dam⁻ strain; available from Tokyo University) because of the restriction enzyme BclI being sensitive to dam, and the plasmid DNA was prepared.

This pLT13 was digested with BclI and dephosphorylated at the 5' ends with bacterial alkaline phosphatase (BAP; Bethesda Research Laboratories).

The following HindIII linker was prepared:

```
GATCAAGCTT
    TTCGAACTAG
```

The two oligonucleotides were phosphorylated at the 5' end with T4 DNA kinase (Takara Shuzo) and then annealed to give the double-stranded DNA.

The BclI digest to pLT13 and the HindIII linker were ligated together in the presence of T4 DNA ligase and the ligation product was introduced into *Escherichia coli* HB101. A plasmid, pLT13H, with the HindIII linker incorporated therein was obtained.

pLT13H was digested with RsrII and HindIII and the digest was fractionated in a conventional manner by 4% acrylamide gel electrophoresis, and a fragment of 502 bp was recovered.

(2) Synthesis of Oligonucleotides

Two oligonucleotides respectively having the structures shown below, namely L1 (88 mer) and L2 (87 mer), were synthesized by the β-cyanoethyl-phosphamide method (Biosearch model 8600). The synthetic oligonucleotides were purified by reversed phase chromatography (C18 column; Waters) in accordance with the Biosearch protocol. After phosphorylation at the 5' end, they were annealed to give a double-stranded DNA.

L1: 5' - CATGCATCTGGCTTCTAACCTGAAACCCGCGGCTCACCTGATCGGT-
GACCCGTCTAAACAGAACTCTCTGCTGTGGCGTGCTAACACG-3'

L2: 5' - GTCCGTGTTAGCACGCCACAGCAGAGAGTTCTGTTTAGACGGGTC-
ACCGATCAGGTGAGCCGCGGGTTTCAGGTTAGAAGCCAGATG-3'

(3) Introduction of LT cDNA Fragment into Expression Vector

The expression vector pKK233-2 (Pharmacia) was digested with NcoI and HindIII, the digest was fractionated in a conventional manner by 0.7% agarose gel electrophoresis, and the vector was recovered. The DNAs prepared in step (1) and step (2) and the above vector were ligated together, the ligation product was introduced into *Escherichia coli* JM105, and selection was performed in LB medium containing ampicillin. About 2,500 transformants were obtained.

(4) Screening with Synthetic Probe

The transformants obtained in step (3) were subjected to the colony hybridization test using, as a probe, the synthetic oligonucleotide L1 prepared in step (2) labeled with [γ-$^{32}$P]ATP at the 5' end. Among the transformants that had hybridized, 24 clones were selected and digested with NsiI (Bethesda Research Laboratories) and RsrII (New England Biolabs). The digests were subjected to agarose gel electrophoresis, and the desired fragment was searched for and the directionality thereof was determined. A plasmid, pDK100, was obtained as the desired one.

(5) Determination of Nucleotide Sequence of Synthetic DNA

The plasmid pDK100 obtained in step (4) was digested with NsiI and HindIII, the digest was fractionated by agarose gel electrophoresis, and the LT cDNA fragment was recovered. This fragment was inserted into M13mp19 between the PstI and HindIII sites, and the base sequence of the synthetic DNA portion was determined by the dideoxy method and found to be in agreement with the desired one.

(6) Introduction of Repressor Gene

The plasmid pMJR1560 (Amersham) was digested with HindIII, the 5' ends were made blunt with DNA polymerase I (Klenow fragment), the blunt-end digest was further digested with EcoRI, the digest obtained was fractionated by 1% agarose gel electrophoresis, and a 1,261-bp fragment containing the lac repressor (lac I$^q$) gene.

Figure 8:
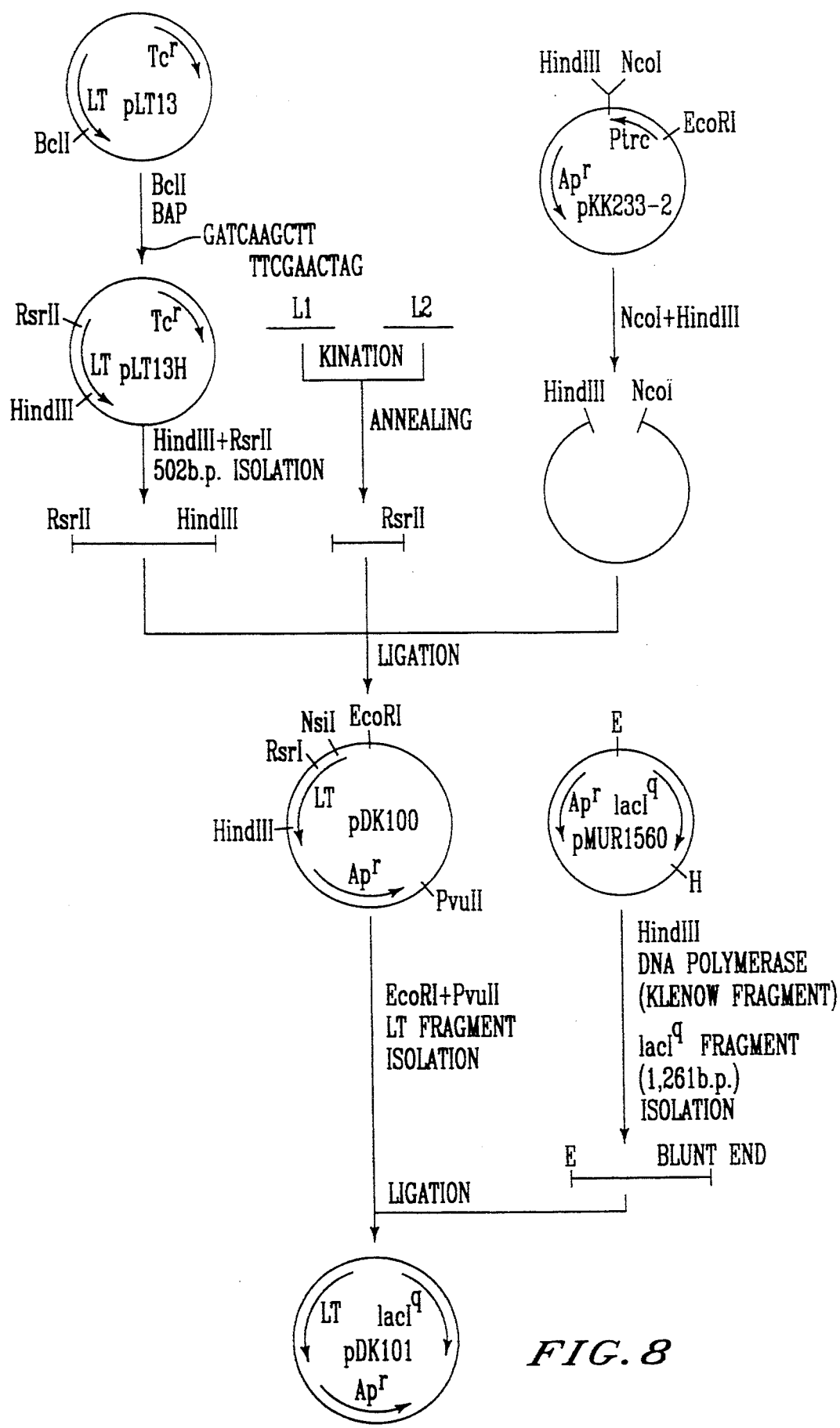
FIG. 8 shows the construction scheme for an expression vector pDK101, which contains a gene coding for the amino acid sequence of the LT polypeptide of Example 15, where the arrow indicates the direction of the action of the promoter.

The plasmid pDK100 obtained in step (4) was digested with EcoRI and PvuII, a fragment containing the LT gene was recovered and ligated with the lac repressor gene-containing fragment, and the ligation product was introduced into *Escherichia coli* HB101. Thus was obtained pDK101. The construction process including the above steps (1) to (6) is shown in FIG. 8.

(7) Introduction into Various *Escherichia Coli* Strains

The DNA of the plasmid pDK101 obtained in step (5) was purified and introduced into *Escherichia coli* JM105, W3110 (ATCC 27325) and Y1089 (ATCC 37196).

EXAMPLE 16

The *Escherichia coli* strains HB101, JM105, W3110 and Y1089 carrying the plasmid pDK101 obtained in step (6) of Example 15 were each cultured in LB-medium (see Note 1 given below) containing 50 μg/ml of ampicillin until the O.D.$_{550\ nm}$ reached 0.5. Then, isopropyl-β-D-thiogalactopyranoside (IPTG) was added to a final concentration of 1 mM, and incubation was continued for further 4 hours. Cells were harvested, washed, suspended in disintegration buffer [50 mM Tris-HCl (pH 8.0), 10 mM EDTA$_{2Na}$, 30 mM NaCl, 0.01 mM (p-amidinophenyl) methanesulfonyl fluoride] and disintegrated by the lysozyme/freezing-thawing method, and the supernatant was assayed for LT activity. The activity data thus obtained are shown in Table 6.

TABLE 6

| Strain (plasmid) | Activity (units/ml) | Specific activity (units/ml OD$_{550}$) |
|---|---|---|
| HB101 (pDK101) | 230,000 | 4.4 × 10$^4$ |
| JM105 (pDK101) | 200,000 | 5.1 × 10$^4$ |
| W3110 (pDK101) | 500,000 | 1.0 × 10$^5$ |
| Y1089 (pDK101) | 210,000 | 4.6 × 10$^4$ |

Note 1: Composition of LB-medium, per liter:Bacto Tryptone 10 g, Bacto yeast extract 5 g, NaCl, 10 g; pH 7 to 7.5.

EXAMPLE 17

The *Escherichia coli* strain W3110 (pDK101) obtained in Example 16 was cultivated by the method of Example 16, and 10 liters of a culture was obtained. This was concentrated by ultrafiltration, and cells were disrupted by means of a high-pressure homogenizer (APV Gaulin). Polyethylenimine (final concentration 0.5%) was added to the homogenate for nucleic acid removal and, then, salting out with ammonium sulfate (40% saturation) was performed. The precipitate obtained was dissolved in 5 mM Tris-HCl buffer (pH 8). The solution was heat-treated at 60° C. for 30 minutes and applied to DEAE-Cellulofine AM column (Chisso Corp.; 9×50 cm) for adsorption. Elution was carried out on a concentration gradient of 0 to 0.2M NaCl. An active fraction was applied to a zinc chelate Sepharose column (Pharmacia; 1.6×20 cm) for adsorption, followed by elution on a concentration gradient of 0 to 0.2M imidazole (pH 7.5). An active fraction (S-200-fractionated fraction). The LT polypeptide in the S-200-fractionated fraction had a specific activity of $7 \times 10^7$ units/mg protein, and the activity recovery from the cell homogenate was 30%. The molecular weight of the LT polypeptide was determined by subjecting the S-200-fractionated fraction to electrophoresis on a 0.1% SDS-containing polyacrylamide gel (SDS-PAGE) [Laemmli, U. K., Nature, 227, 680 [(1970)] and was found to be about 16,000. Furthermore, no decomposition (decrease in molecular weight) of the LT polypeptide was observed in each purification step (SDS-PAGE analysis).

TABLE 7

Amino acid composition of LT polypeptide (III)

| Amino acid | Measured value (moles) | Calculated value based on sequence (III) (moles) |
|---|---|---|
| ILE | 2.9 | 3 |
| VAL | 9.1 | 9 |
| LEU | 21.5 | 21 |
| PHE | 10.1 | 10 |
| CYS | <0.1 | 0 |
| MET | 2.9 | 3 |
| ALA | 11.9 | 12 |
| GLY | 9.0 | 9 |
| THR | 7.1 | 7 |
| TRP | 1.8 | 2 |
| SER | 19.7 | 20 |
| TYR | 6.7 | 7 |
| PRO | 11.5 | 11 |
| HIS | 8.5 | 8 |
| GLU | 11.8 | 2 |
| GLN |  | 10 |
| ASP | 10.1 | 5 |
| ASN |  | 5 |
| LYS | 5.0 | 5 |
| ARG | 2.1 | 2 |

EXAMPLE 18

The S-200-fractionated fraction obtained in Example 17 was purified on C18 reversed-phase chromatography column (Waters; 0.39×30 cm) and the C18-fractionated fraction was submitted to analysis for amino acid composition and analysis for N-terminal amino acid sequence.

(1) Amino Acid Composition

The C18-fractionated fraction was evaporated to dryness under reduced pressure. On a work station (Waters), the solid obtained was hydrolyzed with hydrochloric acid and the hydrolyzate was reacted with phenylisothiocyanate for conversion to PTC-amino acids, and composition analysis was performed using an amino acid analyzer (reversed phase petition method; Waters). Quantitative determination of tryptophan and cysteine was carried out by the method of Inglis, A. S. (Methods in Enzymology, vol. 91, page 26, edited by Hirs, C. H. W. et al. Academic Press, 1983). The results obtained are shown in Table 7.

(2) N-Terminal Amino Acid Sequence

The N-terminal amino acid sequence was determined by Edman's method [Edman, P., Arch. Biochem. Biophys., 22, 475 (1949)] by using a gaseous phase protein sequencer (Applied Biosystems model 477A) and PTH analyzer (Applied Biosystems model 120A).

The thus-found N-terminal amino acid sequence of the LT polypeptide, namely

MET—HIS—LEU—ALA—SER—ASN—LEU—LYS—PRO—ALA—ALA—HIS—LEU—ILE—GLY—ASP—PRO—SER—LYS—GLN—ASN— was in complete agreement with the sequence from the N-terminal amino acid to the 21st amino acid of sequence (III).

EXAMPLE 19

Antitumor activity of LT(III) was evaluated in the same manner as in Example 8' using the S-200-fractionated solution obtained in Example 19. As a result, the tumor disappeared completely on day 25 in the i.v. group and on day 20 in the i.t. group at an LT dose of $1 \times 10^4$ units/mouse/day and of $5 \times 10^2$ units/mouse/day, respectively.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method for the production of a gene which encodes a polypeptide having lymphotoxin activity, which comprises:
   incubating lymphotoxin-producing human T-cell hybridoma A-C5-8 in a medium containing phorbol myristate acetate, concanavalin-A or a mixture thereof, for an incubation time of less than 24 hours;
   fractionating the resulting cells by a sucrose density-gradient centrifugation method;
   isolating a messenger RNA in 12.6S to 14.6S fractions; and preparing a gene from said messenger RNA having the following nucleotide sequence

```
1                    20
CGGGCTCCTGCACCTGCTGCCTGGATCCCCGGCCT 40                   60
GCCTGGGCCTGGGCCTTGGTTCTCCCC

80
ATG ACA CCA CCT GAA CGT CTC TTC CTC CCA AGG 100                  120
GTG TGT GGC ACC ACC CTA CAC CTC CTC CTT CTG
```

```
                    140                 160
GGG CTG CTG CTG GTT CTG CTG CCT GGG GCC CAG

180
GGG CTC CCT GGT GTT GGC CTC ACA CCT TCA GCT 200                      220
GCC CAG ACT GCC CGT CAG CAC CCC AAG ATG CAT 240                    260
CTT GCC CAC AGC AAC CTC AAA CCT GCT GCT CAC

280
CTC ATT GGA GAC CCC AGC AAG CAG AAC TCA CTG 300                    320
CTC TGG AGA GCA AAC ACG GAC CGT GCC TTC CTC

340
CAG GAT GGT TTC TCC TTG AGC AAC AAT TCT 360                      380
CTC CTG GTC CCC ACC AGT GGC ATC TAC TTC GTC 400                      420
TAC TCC CAG GTG GTC TTC TCT GGG AAA GCC TAC

440
TCT CCC AAG GCC ACC TCC TCC CCA CTC TAC CTG 460                      480
GCC CAT GAG GTC CAG CTC TTC TCC TCC CAG TAC 500                    520
CCC TTC CAT GTG CCT CTC CTC AGC TCC CAG AAG

540
ATG GTG TAT CCA GGG CTG CAG GAA CCC TGG CTG 560                      580
CAC TCG ATG TAC CAC GGG GCT GCG TTC CAG CTC 600                      620
ACC CAG GGA GAC CAG CTA TCC ACC ACA CAT GAT

640
GGC ATC CCC CAC CTA GTC CTC AGC CCT AGT ACT 660                      680
GTC TTC TTT GGA GCC TTC GCT CTG TAG AACTTGG 700                720
AAAAATCCAGAAA GAAAAAATAATTGATTTCAAGA
```

```
                    740
CCTTCTCCCCATTCTGCCTCCATTCTGACCATTT 760                780
CAGGGGTCGTCACCACCTCTCCTTTGGCCATTCCAACA 800                      820
GCTCAAGTCTTCCCTGATCAAGTCACCGGAGCTTTC 840                860
AAAGAAGGAATTCTAGGCATCCCAGGGGACCACACC 880                    900
TCCCTGAACCATCCCTGATGTCTGTCTGGCTGAGGA 920                    940
TTTCAAGCCTGCCTAGGAATTCCCAGCCCAAAGCTGTT

960
GGTCTTGTCCACCAGCTAGGTGGGGCCTAGATCCAC 980                     1000
ACACAGAGGAAGAGCAGGCACATGGAGGAGCTT 1020                    1040
GGGGGATGACTAGAGGCAGGGAGGGGACTATTTAT 1060                    1080
GAAGGCAAAAAAATTAAATTATTTATTTATGGAGGAT

1100
GGAGAGAGGGAATAATAGAAGAACATCCAAGGAG 1120                    1140
AAACAGAGACAGGCCCAAGAGATGAAGAGTGAGA 1160                    1180
GGGCATGCGCACAAGGCTGACCAAGAGAGAAAGAA

1200
GTAGGCATGAGGGATCACAGGGCCCCAGAAGG 1220                    1240
CAGGGAAAGGCTCTGAAAGCCAGCTGCCGACCAGAG 1260                    1280
CCCCAAACGGAGGCATCTGCATCCTCGATGAAGCC 1300           1310
CAATAAACCTCTTTTCTCCCCCT
``` wherein a part of said nucleotide sequence encodes a polypeptide having lymphotoxin-activity.

2. The method of claim 1, wherein said incubation time is less than 8 hours.

* * * * *

UNITED STATES PATENT AND TRADEMARK OFFICE
CERTIFICATE OF CORRECTION

PATENT NO. : 5,403,725
DATED : April 4, 1995
INVENTOR(S) : Toshiaki OSAWA, et al.

It is certified that error appears in the above-indentified patent and that said Letters Patent is hereby corrected as shown below:

On the title page, Item [75], the fourth inventor's name should read:

--Yoshiro Kobayashi--

Signed and Sealed this

Twentieth Day of June, 1995

Attest:

BRUCE LEHMAN

*Attesting Officer*   *Commissioner of Patents and Trademarks*